US007282225B1

(12) United States Patent
Davis et al.

(10) Patent No.: US 7,282,225 B1
(45) Date of Patent: Oct. 16, 2007

(54) COMPOSITION AND METHODS FOR IMPROVING RETINAL HEALTH

(75) Inventors: Richard Davis, El Dorado Hills, CA (US); Howard L. Howell, Clearwater, FL (US)

(73) Assignee: Occular Technologies, Inc., Clearwater, FL (US)

( * ) Notice: Subject to any disclaimer, the term of this patent is extended or adjusted under 35 U.S.C. 154(b) by 0 days.

(21) Appl. No.: 11/528,012

(22) Filed: Sep. 27, 2006

(51) Int. Cl.
*A01N 65/00* (2006.01)

(52) U.S. Cl. ............... 424/725; 424/764; 424/732

(58) Field of Classification Search ............ None
See application file for complete search history.

(56) References Cited

U.S. PATENT DOCUMENTS

| | | | |
|---|---|---|---|
| 2,858,215 A | 10/1958 | Espoy et al. |
| 3,608,083 A | 9/1971 | Bunnell et al. |
| 3,856,941 A | 12/1974 | Turner |
| 4,296,130 A | 10/1981 | Herschler |
| 4,342,784 A | 8/1982 | Havemeyer et al. |
| 4,477,469 A | 10/1984 | Herschler |
| 4,486,435 A | 12/1984 | Schmidt et al. |
| 4,603,143 A | 7/1986 | Schmidt |
| 4,708,965 A | 11/1987 | Morgan |
| 4,717,561 A | 1/1988 | Krivak et al. |
| 4,772,591 A | 9/1988 | Meisner |
| 4,863,748 A | 9/1989 | Herschler |
| 4,933,184 A | 6/1990 | Tsuk |
| 4,938,969 A | 7/1990 | Schinitsky et al. |
| 4,973,605 A | 11/1990 | Herschler |
| 5,071,878 A | 12/1991 | Herschler |
| 5,118,505 A | 6/1992 | Koltringer |
| 5,156,852 A | 10/1992 | La Haye et al. |
| 5,196,417 A | 3/1993 | Dolling et al. |
| 5,229,130 A | 7/1993 | Sharma et al. |
| 5,238,933 A | 8/1993 | Catz et al. |
| 5,254,343 A | 10/1993 | Parah et al. |
| 5,266,594 A | 11/1993 | Dawson et al. |
| 5,281,722 A | 1/1994 | Blaschke et al. |
| 5,306,731 A | 4/1994 | Epstein |
| 5,310,764 A | 5/1994 | Baranowitz et al. |
| 5,334,612 A | 8/1994 | Kalden et al. |
| 5,409,693 A | 4/1995 | Perricone |
| 5,432,199 A | 7/1995 | Cavazza |
| 5,449,688 A | 9/1995 | Wahl et al. |
| 5,457,135 A | 10/1995 | Baranowitz et al. |
| 5,468,476 A | 11/1995 | Ahluwalia et al. |
| 5,470,874 A | 11/1995 | Lerner |
| 5,482,965 A | 1/1996 | Rajadhyaksha |
| 5,532,269 A | 7/1996 | Koltringer |

(Continued)

FOREIGN PATENT DOCUMENTS

EP          0 595 005          5/1994

(Continued)

*Primary Examiner*—Patricia Leith
*Assistant Examiner*—Qiuwen Mi
(74) *Attorney, Agent, or Firm*—McCarter & English, LLP

(57) ABSTRACT

The present invention relates to a nutritional dietary supplement composition comprising a combination of effective amounts of vitamins, minerals, carotenoids, antioxidants, natural herbal extracts in an inert stabilizing carrier, which stabilizes and or enhances visual function and acuity. The present invention also relates to methods for treating or preventing macular degeneration comprising administering an effective amount of the dietary supplement composition of the invention.

14 Claims, 6 Drawing Sheets

U.S. PATENT DOCUMENTS

| | | |
|---|---|---|
| 5,545,614 A | 8/1996 | Stamler et al. |
| 5,569,670 A | 10/1996 | Weischer et al. |
| 5,571,441 A | 11/1996 | Andon et al. |
| 5,585,402 A | 12/1996 | Moncada et al. |
| 5,596,011 A | 1/1997 | Repine et al. |
| 5,620,980 A | 4/1997 | Samour |
| 5,643,587 A | 7/1997 | Scancarella et al. |
| 5,650,429 A | 7/1997 | Conrad et al. |
| 5,665,757 A | 9/1997 | Dunn et al. |
| 5,667,791 A | 9/1997 | Hersh et al. |
| 5,676,956 A | 10/1997 | Duffy et al. |
| 5,691,380 A | 11/1997 | Mason et al. |
| 5,723,451 A | 3/1998 | Majalli et al. |
| 5,728,735 A | 3/1998 | Ulrich et al. |
| 5,747,536 A | 5/1998 | Cavazza |
| 5,766,873 A | 6/1998 | Noble et al. |
| 5,780,693 A | 7/1998 | Bernhard et al. |
| 5,786,342 A | 7/1998 | Carpenter et al. |
| 5,789,396 A | 8/1998 | Blank et al. |
| 5,792,449 A | 8/1998 | Bryce-Smith |
| 5,804,594 A | 9/1998 | Murad |
| 5,804,597 A | 9/1998 | Yamakoshi et al. |
| 5,807,957 A | 9/1998 | Samour et al. |
| 5,821,237 A | 10/1998 | Bissett et al. |
| 5,824,659 A | 10/1998 | Strickland et al. |
| 5,837,289 A | 11/1998 | Grasela et al. |
| 5,846,996 A | 12/1998 | Fallick |
| 5,871,769 A | 2/1999 | Fleming et al. |
| 5,873,831 A | 2/1999 | Bernstein et al. |
| 5,876,736 A | 3/1999 | Cohen et al. |
| 5,883,128 A | 3/1999 | Yu et al. |
| 5,886,042 A | 3/1999 | Yu et al. |
| 5,889,054 A | 3/1999 | Yu et al. |
| 5,897,891 A | 4/1999 | Godfrey |
| 5,916,912 A | 6/1999 | Ames et al. |
| 5,922,331 A | 7/1999 | Mausner |
| 5,922,346 A | 7/1999 | Hersh |
| 5,925,348 A | 7/1999 | Riley et al. |
| 5,925,381 A | 7/1999 | Boyle et al. |
| 5,925,620 A | 7/1999 | Ohlenschlager et al. |
| 5,937,790 A | 8/1999 | Ito et al. |
| 5,939,394 A | 8/1999 | Fleming et al. |
| 5,945,447 A | 8/1999 | Fallick |
| 5,948,443 A | 9/1999 | Riley et al. |
| 5,955,102 A | 9/1999 | Gorenbein et al. |
| 5,997,915 A | 12/1999 | Bailey et al. |
| 6,030,645 A | 2/2000 | Tritsch et al. |
| 6,103,756 A | 8/2000 | Gorsek |
| 6,207,190 B1 * | 3/2001 | Richardson et al. ........ 424/472 |
| 6,329,432 B2 | 12/2001 | Howard et al. |
| 6,339,102 B1 | 1/2002 | Meyerhoff et al. |
| RE38,009 E | 2/2003 | Garnett et al. |
| 6,579,544 B1 | 6/2003 | Rosenberg et al. |
| 6,582,721 B1 * | 6/2003 | Lang .......................... 424/439 |
| 6,649,195 B1 | 11/2003 | Gorsek |
| 6,660,297 B2 | 12/2003 | Bartels et al. |
| 7,029,712 B1 * | 4/2006 | Thornton et al. ........... 424/756 |
| 2005/0031761 A1 * | 2/2005 | Brucker et al. ............. 426/595 |
| 2006/0034954 A1 * | 2/2006 | Bland et al. ................ 424/757 |
| 2006/0127505 A1 | 6/2006 | Haines et al. |
| 2006/0134226 A1 | 6/2006 | Leonard |
| 2006/0135610 A1 | 6/2006 | Bortz et al. |

FOREIGN PATENT DOCUMENTS

| | | | |
|---|---|---|---|
| EP | 0 867 177 | | 2/1998 |
| KR | 2006087846 | * | 8/2006 |
| WO | 92/05780 | | 4/1992 |
| WO | WO 200191770 | * | 6/2001 |

* cited by examiner

COMPOSITION AND METHODS FOR IMPROVING RETINAL HEALTH

FIELD OF THE INVENTION

The present invention relates to a nutritional dietary supplement composition and related methods of administration for the treatment and/or prevention of retinal diseases, and their concomitant impairment of vision. In particular, the invention relates to a nutritional supplement comprising a combination of ingredients useful for treating and/or preventing macular degeneration.

BACKGROUND OF THE INVENTION

Age-related macular degeneration (AMD) is an eye disease that affects the central part of the retina and is the leading cause of vision loss and blindness in people over the age of 50 in the U.S. AMD affects an estimated 15 million people in North America alone, and causes severe vision impairment in about 1.2 million of these patients. About 30% of US patients over the age of 75 have some form of AMD, and 23% of the remainder will develop it within five years. Generally, the prevalence of AMD increases with age from 16.8% in patients ages 55-64 to 25.6% in patients ages 65-74 and up to 42% in patients over age 75 in some societies.

Macular degeneration is a disorder which is often characterized as one of two types: (a) non-exudative (the dry form); or (b) exudative (the wet form). Although many theories abound, there is no known cause of AND, neither is there currently any known cure for the dry or atrophic form of AMD. Dry AMD is characterized by hard or soft drusen (deposits of cellular debris), changes in the retinal pigment epithelium (RPE), or atrophy of photoreceptors and RPE. The dry form accounts for approximately 90% of all AMD cases; the remainder being diagnosed with the "wet" form of AMD. Wet AMD is characterized by neovascularization and exudative changes in the retina. Although both types are bilateral and progressive, each type may reflect different pathological processes. With few exceptions however, non-exudative AMD almost always precedes the development of exudative AMD.

Both exudative (wet form) and non-exudative (dry form) macular degeneration are typically accompanied by the formation of drusen. Drusen are characterized by irregular, discrete, round yellow-white deposits which accumulate in the retina (back of the eye) between the basement membrane of the RPE and the rest of Bruch's membrane. The presence of drusen most likely reflects abnormalities in retinal pigment epithelial function. Drusen deposits can be further characterized into hard drusen or soft drusen. Hard or nodular drusen derive from debris accumulation from retinal pigment epithelial cells in Bruch's membrane. Soft drusen are usually larger than hard drusen and have soft, indistinct margins. Soft drusen are small detachments of the retinal pigment epithelium and presumably derive from diffuse retinal pigment epithelial dysfunction. Soft drusen can also derive from diffuse or confluent drusen, which further derive from a thickening of the inner portion of Bruch's membrane. Calcified drusen are characterized by a glistening appearance and are the consequence of calcification of nodular and diffuse drusen formations.

The non-exudative (dry form) macular degeneration ("D-AMD") involves atrophy and degeneration of the outer retina, retinal pigment epithelium, Bruch's membrane, and choriocapillaris. The resultant effects of non-exudative macular degeneration are formation of drusen, pigmentary changes, and atrophy. Dysfunction of the retinal pigment epithelium, in particular, leads to the loss of photoreceptors, which are metabolically dependent on the retinal pigment epithelium. Vision loss in dry AMD is typically slowly progressive.

Exudative (wet form) macular degeneration is characterized by serous or hemorrhagic separation of the retinal pigment epithelium or neurosensory layer. Patients may develop choroidal neovascularization, which is manifested as fluid accumulation, hemorrhage, and/or lipid exudation. Vision loss can be rapid. These defects typically cause metamorphopsia (distortion) which is detected clinically by Amsler grid testing. An Amsler grid consists of a chart with lines forming small squares. When choroidal neovascularization is manifested as fluid accumulation, hemorrhage, and/or lipid exudation the vision is distorted and the lines making up the squares of the grid become blurred and/or wavy.

Choroidal neovascularization occurs by vessels from the choroidal membrane growing through Bruch's membrane into the subretinal pigment epithelial or subretinal space. This in itself can lead to severe visual loss, however, the retinal pigment epithelium or the neurosensory retina may also detach. Patients with pigment epithelial detachments may develop associated choroidal neovascular membranes. Even with no choroidal neovascular membranes present, 40% of patients with pigment epithelial detachments may continue to experience further loss of vision. Affected patients may exhibit metamorphopsia by Amsler grid testing. Further consequences of exudative macular degeneration can include tearing of the retinal pigment epithelium and often development of a disciform scar with associated photoreceptor degeneration.

Both of the above-described forms of macular degeneration (non-exudative and exudative) usually proceed continuously toward irreversible loss of central vision. Ultimately, the retina is damaged by long-standing edema, underlying hemorrhage, and/or detachment. Following detachment, the retina may undergo fibrosis, metaplasia, elevation and scarring.

A number of therapies have recently been introduced for the treatment of wet AMD which target the inhibition of certain underlying angiogenesis processes, but at present there is no effective treatment for non-exudative macular degeneration that has been proven in its ability to enhance vision in a large clinical trial. Management of non-exudative macular degeneration is limited to early diagnosis and careful follow-up to determine if the patient develops choroidal neovascularization. In addition, intervention with diet, exercise and dietary supplement programs are frequently instituted.

However, the dietary supplements in use today have not demonstrated an ability to reliably slow the rate of progression in the vision loss or prevent AMD. Also, none of the supplements in use today have undergone the rigorous testing and demanding controls encountered within the context of an FDA-regulated clinical trial. Therefore, there exists a currently unmet need in the art for a proven effective dietary supplement composition and method to treat and/or prevent AMD, in particular D-AMD, which afflicts 90% of patients with AMD. Thus, a treatment means that can effectively stabilize and/or enhance the visual function of patients diagnosed with the dry form of AMD would be of considerable benefit; especially if patients and physicians could point to the results of such a treatment that occurred within the context of a rigorous randomized prospective controlled clinical trial. The present invention discloses such a tested composition and method.

SUMMARY OF THE INVENTION

The present invention is based on the discovery that the combination of nutrient components, as disclosed in the embodiments described herein, provides an effective treatment for the dry form of age-related macular degeneration. The specific and unique combination of vitamins, minerals, carotenoids, antioxidants, and other nutrients in the amounts specified stabilizes and/or enhances visual function in a significant number of patients with the dry form of AMD. The efficacy of the present invention has been demonstrated by testing in a clinical trial that followed randomized patients for a period of 12-months post-baseline. While not being limited to any particular theory, the inventors hypothesize that the vision-preserving and enhancing effects of the present invention are derived from synergies occurring from the combination of effective amounts of specific vitamins, minerals, anti-oxidants and other nutrients. As such, the present invention is distinguished from the currently available dietary supplements, which have been unable to demonstrate a clinically significant stabilization and/or improvement of vision in the rigorous context of a multi-center, randomized prospective, controlled clinical trial.

Therefore, in one aspect the invention relates to a dietary supplement composition and formulation for enhancing retinal health. In another aspect, the invention relates to a dietary supplement composition for treating and/or preventing AMD. In a preferred embodiment, the invention comprises a composition for treating and/or prevention AMD-related vision loss in an individual with the dry form of AMD. In addition, the present invention relates to compositions, which administered in an effective amount to an individual in need thereof, can enhance vision and improve their quality of life.

In another aspect, the invention relates to methods for enhancing retinal health, treating and/or preventing AMD, and treating and/or preventing AMD-related vision loss comprising administering an effective amount of the composition of the invention to an individual in need thereof. In certain embodiments, the invention relates to methods for treating and preventing the onset or progression of exudative and non-exudative macular degeneration. In particular the composition and methods are effective for treating the non-exudative form (dry form) of the disease for which there has been little effective treatment. It is believed that the composition of the invention is efficacious, in part, because of a unique combination of materials and/or formulation methods.

In still another aspect, the present invention relates to a dietary supplement formulation which has been demonstrated to be safe and effective in the context of a clinical trial to stabilize and enhance vision in patients with the dry form of AMD.

In any of the aspects or embodiments described herein, an effective amount of the dietary supplement composition of the present invention may be administered at least once daily, and in any pharmaceutically acceptable dosage form known or which becomes known by those of skill in the art. In addition, the dietary supplement can be administered by any pharmaceutically acceptable route recognized by those of skill in the art, for example, oral, enteral, parenteral, intravenous, transdermal, nasal, rectal, topical, or the like. In a preferred embodiment, the dietary supplement of the invention is a unitary dosage form suited for oral administration or consumption by an individual at least once per day, for example, in a capsule, tablet, caplet, soft gel capsule, controlled release tablet, powder, liquid, liquid or gel filled capsule, and the like.

DETAILED DESCRIPTION OF THE INVENTION

Figure 1:
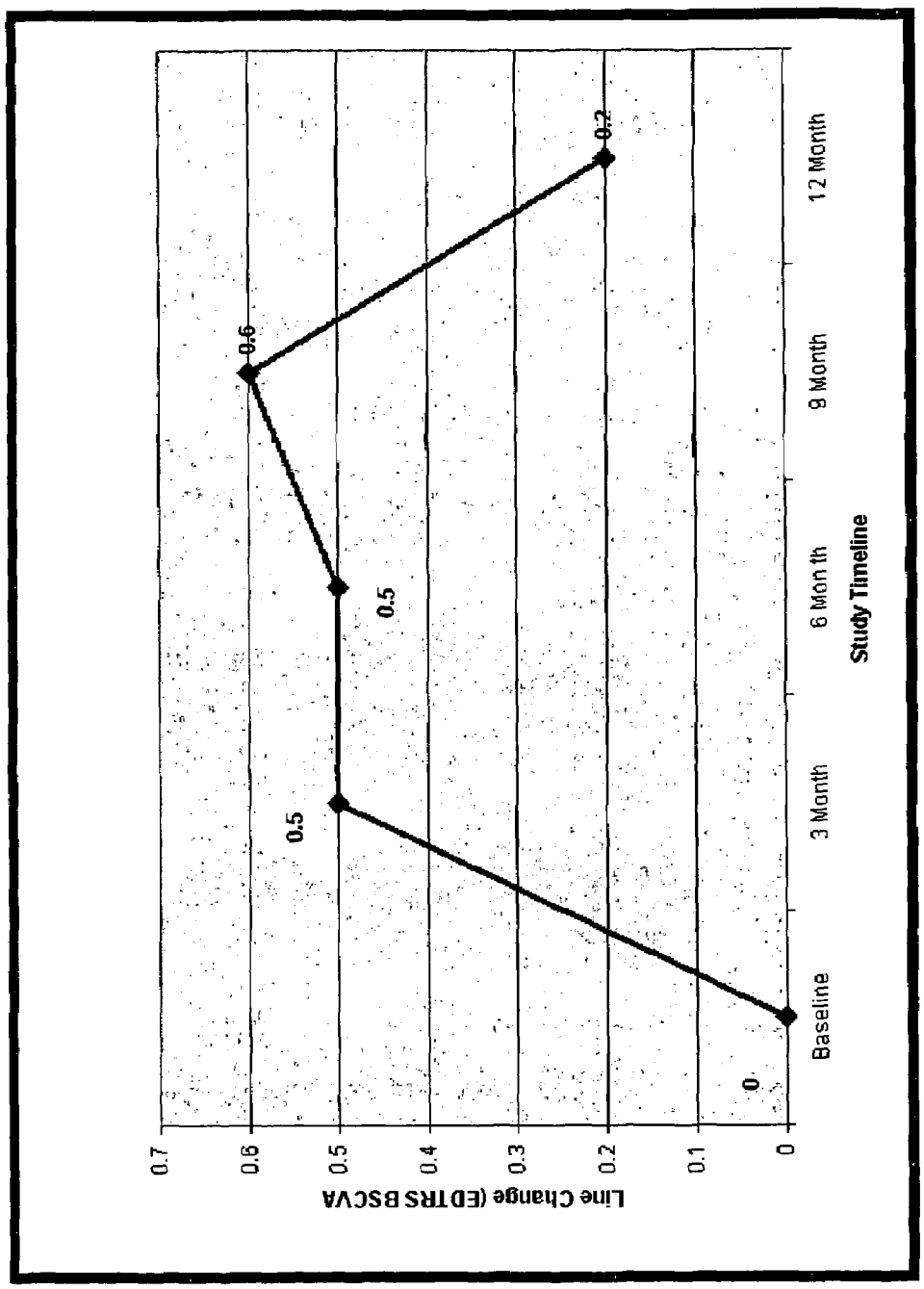
FIG. 1. Change in ETDRS BSCVA Vision Over Time. Line graph plot of best spectacle-corrected visual acuity (BSCVA) vs. time, showing the mean LogMAR change in early treatment diabetic retinopathy scale (ETDRS) vision as measured by the standardized ETDRS method of determining the BSCVA for all study eyes in all patients in the modified per protocol analysis who took the dietary supplement of the invention as the only active treatment being obtained in the control group of the clinical trial (herein, the "MIRA-1" trial) as measured over the 12-month duration of the study.
Figure 2:
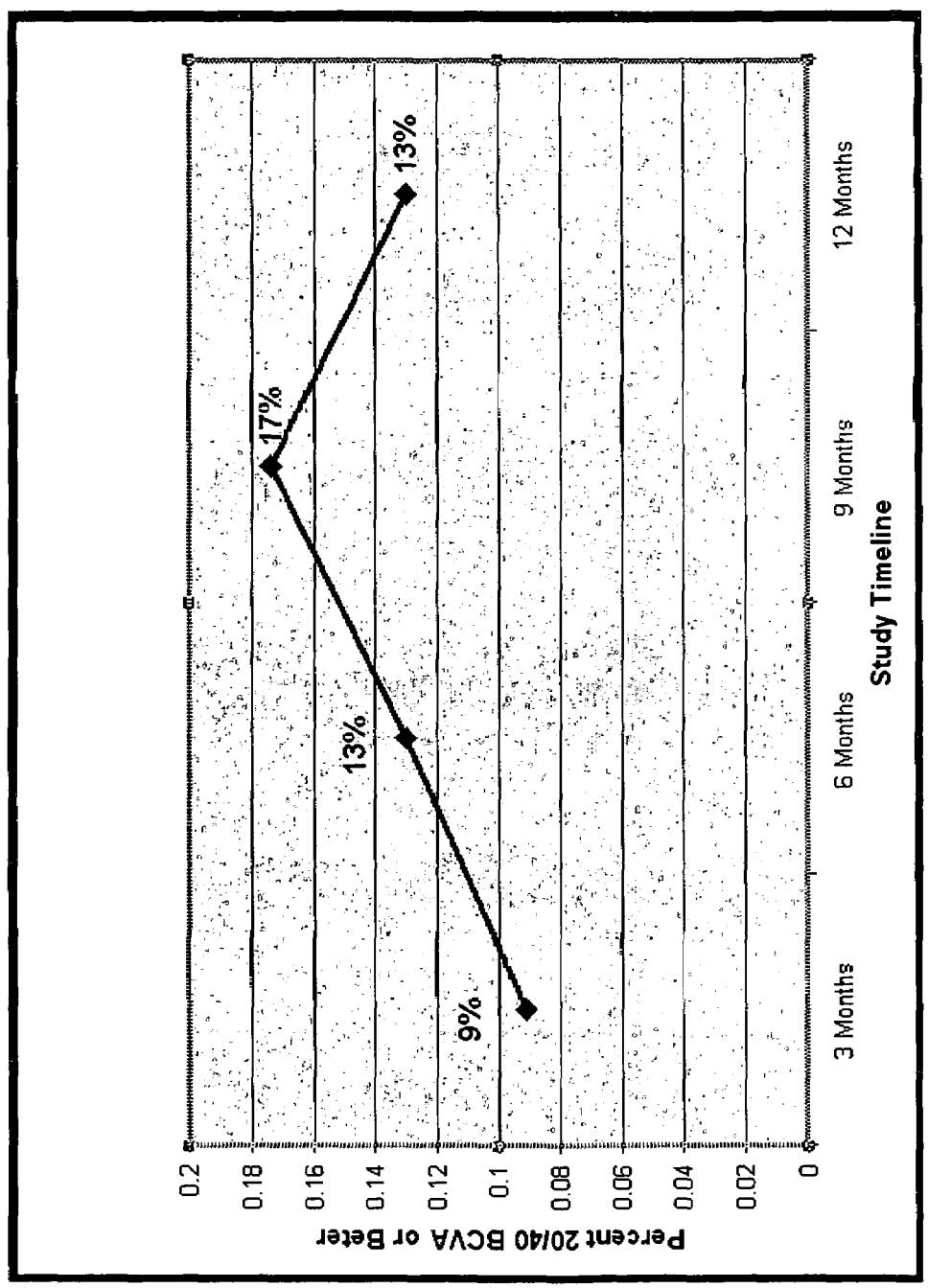
FIG. 2. Return to 20/40 Vision. Line graph plot of the percent of those eyes with baseline BSCVA vision worse than 20/40 that improved to BSCVA 20/40 or better as measured by the standardized ETDRS method of determining the BSCVA for all study eyes in all patients in the modified per protocol analysis who took the dietary supplement of the invention as the only active treatment being obtained by the control group in the MIRA-1 trial as measured over the 12-month duration of the study.
Figure 3:
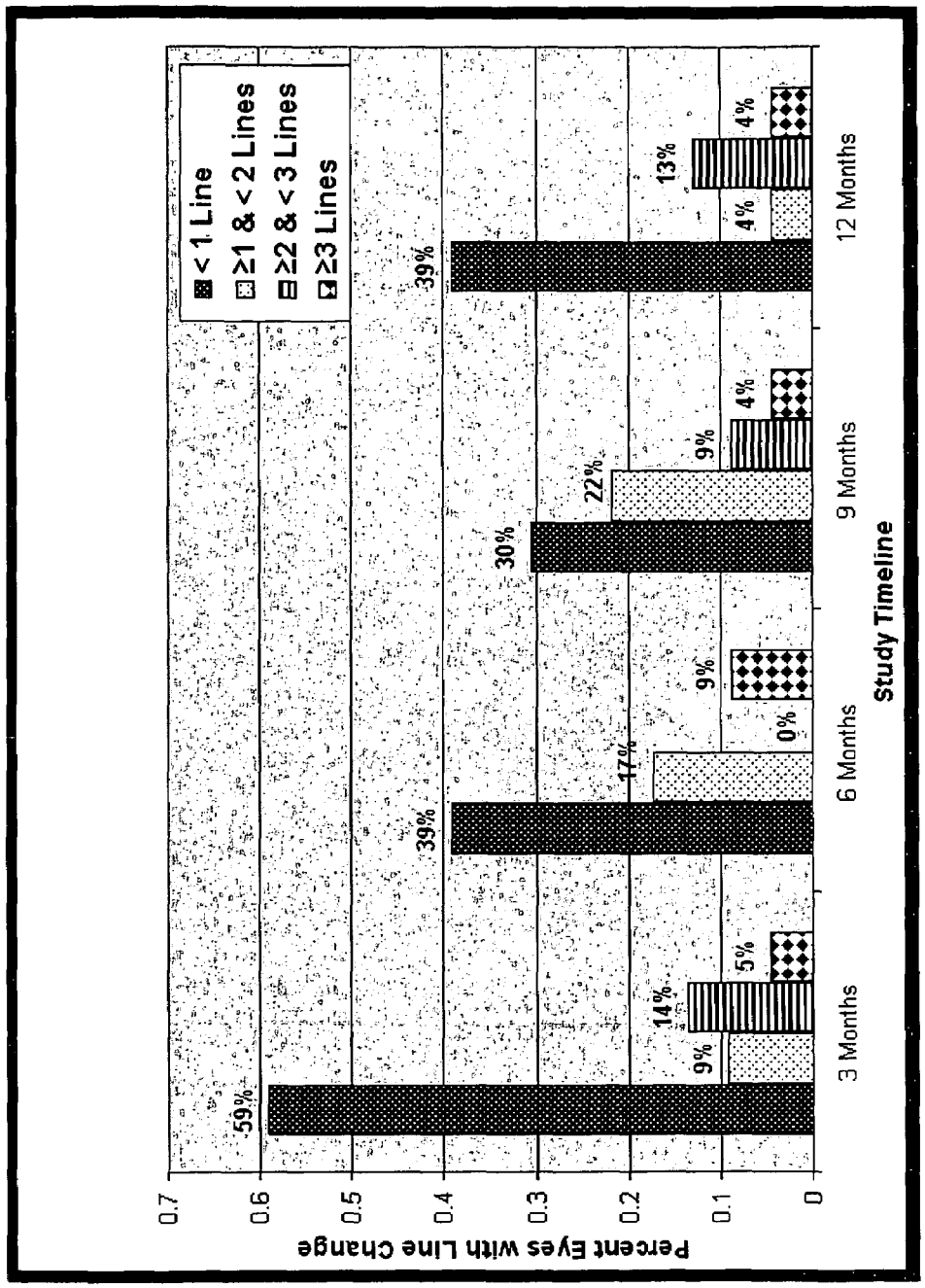
FIG. 3. Analysis of ETDRS BSCVA Vision Improvement. Bar graph showing the percentage breakdown of absolute LogMAR vision improvement in all study eyes in all patients in the modified per protocol analysis over the 12-month study as measured by lines of ETDRS vision change of all patients taking the dietary supplement of the invention in the MIRA-1 Trial. The absolute vision improvement is displayed as a percentage of all aforesaid eyes in the total patient population taking the dietary supplement of the invention as the only active treatment being obtained in the control group of the MIRA-1 study organized by: (a) a gain of 3 or more lines of vision; (b) gain of 2 or more lines but less than 3 lines of vision; (c) gain of 1 or more lines but less than 2 lines of vision; (d) gain of up to 1 line of vision.
Figure 4:
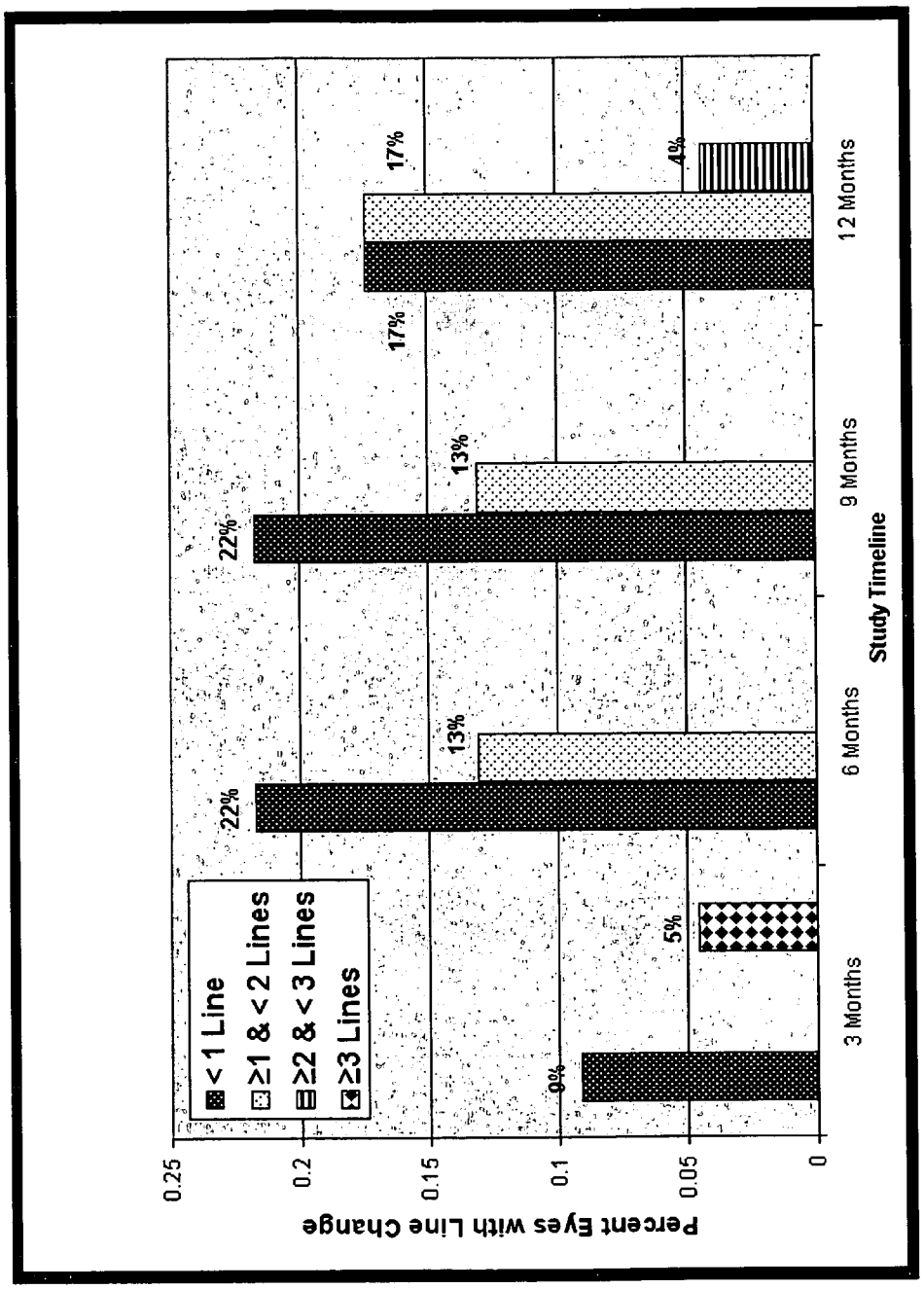
FIG. 4. Analysis of ETDRS BSCVA Vision Loss. Bar graph showing the percentage breakdown of absolute LogMAR vision loss in all study eyes in all patients in the modified per protocol analysis over the 12-month study as measured by lines of ETDRS vision change of all patients taking the dietary supplement of the invention in the MIRA-1 Trial. The absolute vision loss is displayed as a percentage of all aforesaid eyes in the total patient population taking the dietary supplement of the invention as the only active treatment being obtained in the control group of the MIRA-1 study organized by: (a) a loss of 3 or more lines of vision; (b) loss of 2 or more lines but less than 3 lines of vision; (c) loss of 1 or more lines but less than 2 lines of vision; (d) loss of up to 1 line of vision.
Figure 5:
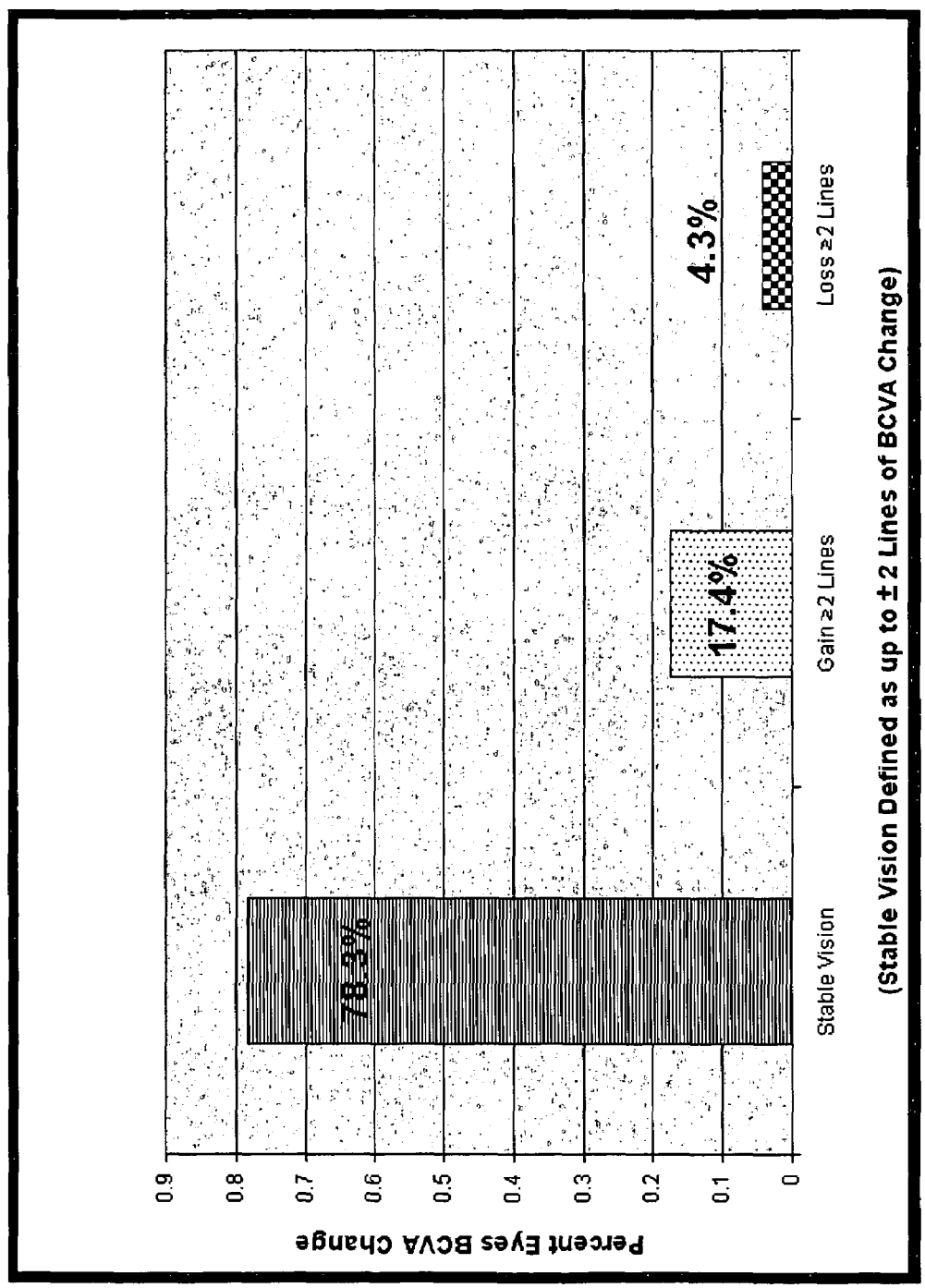
FIG. 5. Summary of Vision Change at 12-Months Post Baseline. Bar graph showing the percentage breakdown summary of absolute LogMAR vision change in all study eyes in all patients in the modified per protocol analysis over the 12-month study as measured by lines of ETDRS vision change of all patients taking the dietary supplement of the invention in the MIRA-1 Trial. The absolute vision change is displayed as a percentage of all aforesaid eyes in the total patient population taking the dietary supplement of the invention as the only active treatment being obtained in the control group of the MIRA-1 study organized by: (a) Stable Vision; (b) Gain of 2 or more lines of vision; (c) loss of 2 or more lines of vision.

The macula is responsible for acute central vision and is composed of light-sensing cells (some rods and predominantly cones) while the underlying retinal pigment epithelium (RPE) and choroids nourish and help remove waste materials. The RPE nourishes the cones with the vitamin A substrate for the photosensitive pigments and digests the cones shed outer tips. RPE is exposed to high levels of UV radiation, and secretes factors that inhibit angiogenesis. The choroid contains a dense vascular network that provides nutrients and removes the waste materials.

In AMD, the shed cone tips become indigestible by the RPE, where the cells swell, undergo senescence and ultimately die after collecting too much undigested material. Collections of undigested waste material, called drusen, form under the RPE. Photo-toxic damage also causes the accumulation of lipofuscin in RPE cells. The intracellular lipofuscin and accumulation of drusen in Bruch's membrane interferes with the transport of oxygen and nutrients to the retinal tissues, and ultimately leads to RPE and photoreceptor dysfunction. In exudative AMD, blood vessels grow from the choriocapillaris through defects in Bruch's membrane and may grow under the RPE, detaching it form the choroids, and leaking fluid or bleeding which can cause a sudden and profound loss of vision.

The present invention relates to a dietary supplement composition for improving retinal health comprising an effective amount of vitamins, antioxidants, carotenoids, and other nutrients. With reference to Table 1; in certain embodiments the composition comprises an effective amount of vitamins A, C, and E; a carotenoid; a mineral, such as copper; zinc; and selenium; alpha lipoic acid; and at least one additional member selected from the group consisting of boron, chloride, iodine, nickel, phosphorous, potassium, silicon, tin, vanadium; an herbal extract, for example, marigold extract, alfalfa (grass powder), bilberry extract, eyebright (herb powder), spinach (leaf powder), citrus bioflavanoid complex, lutein, and zeaxanthin. The unexpected and surprising discovery that the composition of the invention demonstrates clinically significant efficacy suggests that the components of the composition of the invention work synergistically to effectuate an improvement in clinical outcome.

In any of the preferred embodiments the composition of the invention also comprises at least one of the following: a stabilizer or carrier, for example, cellulose, magnesium stearate, silica; a lipid; an oil; a salt; an acid; a base; an emulsifier; an excipients; a flavoring agent; or combinations thereof.

The pigment of the macula, which is one of the protective factors that prevent sunlight from damaging the retina, is formed by the accumulation of nutritionally derived carotenoids, such as lutein, the yellow pigment that serves as a delivery vehicle for other important nutrients and zeaxanthin. Antioxidants such as vitamins C, and E, beta-carotene, and lutein as well as zinc, selenium, and copper are all found in the healthy macula. In addition to providing nourishment, these antioxidants protect against free radical damage that many believe may be one of the causative factors involved with the development of age-related macular degeneration.

In certain embodiments the invention comprises a method for enhancing retinal health comprising administering an effective amount of the composition of the invention to an individual in need thereof. In a related embodiment, the invention comprises a method for treating and/or preventing vision loss in individuals, treating and/or prevent the onset or progression of exudative and non-exudative macular degeneration, and/or treating the non-exudative form (dry form) of AMD. In any of the above methods, the invention comprises the steps of administration of an effective amount of the composition of the invention to an individual in need thereof.

The components of the composition of the invention are described in detail below and with reference to Table 1, which shows the components and formulation of one of the preferred embodiments of the invention.

Vitamin A

In one embodiment of the composition of the present invention the dietary supplement comprises a daily dose of from about 2500 IU to about 6000 IU of vitamin A. In a preferred embodiment, the dietary supplement of the invention comprises from about 4500 IU to about 5500 IU of vitamin A. In the most preferred embodiment, the invention comprises about 5000 IU of vitamin A. In certain embodiments the vitamin A is present as 2500 IU of retinyl palmitate, and 2500 IU of beta-carotene, a provitamin A carotenoid. Vitamin A is commercially available, for example, as Betatene™ 7.5% (Cognis Corp.; Cincinnati, Ohio), which has 119 IU/mg. This combination of direct vitamin and provitamin administration is designed to maximize the clinical effectiveness, bioavailability and potency in and among the other components of the composition while still providing a comfortable safety margin to achieve the vision stabilization and enhancement objects of the present invention—as such are documented in the unexpected results of the MIRA-1 clinical trial as described herein. Also, since certain malignancies have been associated with high doses of vitamin A, the present formulation is designed to minimize this risk.

Vitamin A is a family of fat-soluble compounds that play an important role in vision, bone growth, reproduction, cell division, and cell differentiation (in which a cell becomes part of the brain, muscle, lungs, etc . . . ). Vitamin A helps regulate the immune system, which helps prevent or fight off infections by making white blood cells that destroy harmful bacteria and viruses. Vitamin A also may help lymphocytes, a type of white blood cell, fight infections more effectively.

Vitamin A promotes healthy surface linings of the eyes and the respiratory, urinary, and intestinal tracts. When those linings break down, it becomes easier for bacteria to enter the body and cause infection. Vitamin A also helps maintain the integrity of skin and mucous membranes, which also functions as a barrier to bacteria and viruses.

Retinol is one of the most active, or usable forms of vitamin A, and is found in animal foods such as liver and whole milk and in some fortified food products. Retinol is also called preformed vitamin A. It can be converted to retinal and retinoic acid, other active forms of the vitamin A family.

Provitamin A carotenoids are darkly colored pigments found in plant foods that can be converted to vitamin A. In the United States, approximately 26% to 34% of vitamin A consumed by men and women, respectively, is provided by provitamin A carotenoids. Common carotenoids found in foods are alpha-carotene, beta-carotene, lutein, zeaxanthin, lycopene, and cryptoxanthin. Of the 563 identified carotenoids, fewer than 10% are precursors for vitamin A. Among these, beta-carotene is most efficiently converted to retinol. Alpha-carotene and beta-carotene are also converted to vitamin A, but only half as efficiently as beta-carotene. Lycopene, lutein, and zeaxanthin are carotenoids that do not have vitamin A activity but have other health promoting properties as will be discussed herein.

Some carotenoids, in addition to serving as sources of vitamin A, have been shown to function as antioxidants in laboratory tests. However, this role has not been consistently demonstrated in humans. Antioxidants protect cells from free radicals, which are potentially damaging by-products of oxygen metabolism that may contribute to the development of some chronic diseases including age-related macular degeneration. Vitamin A has demonstrated a significant protective effect against light-induced damage.

Recommendations for vitamin A are provided in the Dietary Reference Intakes (DRIs) developed by the Institute of Medicine (1OM). DRI is the general term for a set of reference values used for planning and assessing nutrient intake in healthy people. Three important types of reference values included in the DRIs are the Recommended Dietary Allowances (RDA), Adequate Intake (AI), and Tolerable Upper Intake Levels (UL). The RDA recommends the average daily dietary intake level that is sufficient to meet the nutrient requirements of nearly all (97-98%) healthy individuals in each age and gender group. An AI is set when there are insufficient scientific data to establish a RDA. AIs meet or exceed the amount needed to maintain nutritional adequacy in nearly all people. The UL, on the other hand, is the maximum daily intake unlikely to result in adverse health effects.

In Table 2, below, the RDAs for vitamin A are listed as micrograms (mgs) of retinol activity equivalents (RAE) to account for the different biological activities of retinol and provitamin A carotenoids. The table also lists RDAs for vitamin A in International Units (IUs), which are used on food and supplement labels (1 RAE=3.3 IU).

TABLE 2

Recommended Dietary Allowances (RDAs) for Vitamin A.

| Age (Years) | Children (µg RAE) | Males (µg RAE) | Females (µg RAE) | Pregnancy (µg RAE) | Lactation (µg RAE) |
|---|---|---|---|---|---|
| 1-3 | 300 (1000 IU) | | | | |
| 4-8 | 400 (1320 IU) | | | | |
| 9-13 | 600 (2000 IU) | | | | |
| 14-18 | | 900 (3000 IU) | 700 (2310 IU) | 750 (2500 IU) | 1200 (4000 IU) |
| 19+ | | 900 (3000 IU) | 700 (2310 IU) | 750 (2565 IU) | 1300 (4300 IU) |

There is no RDA for beta-carotene or other provitamin A carotenoids. The IOM states that consuming 3 to 6 mg of beta-carotene daily (equivalent to 833-1667 IU vitamin A) will maintain blood levels of beta-carotene in the range associated with a lower risk of chronic diseases; including age-related macular degeneration.

Vitamin E

In one embodiment of the composition of the present invention the dietary supplement comprises a daily dose of from about 50 IU to about 800 IU of vitamin E (as D,L-alpha tocopherol acetate). In a preferred embodiment, the dietary supplement of the invention comprises from about 20 IU to about 600 IU of vitamin E. In the most preferred embodiment, the invention comprises about 400 IU of vitamin E. This amount is designed to maximize the clinical effectiveness, bioavailability, and potency synergies in and among the other components of the present invention, while still providing a comfortable safety margin to achieve vision stabilization and enhancement.

Vitamin E is a fat-soluble vitamin that exists in eight different forms. Each form has its own biological activity, which is the measure of potency or functional use in the body. Alpha-tocopherol (alpha-tocopherol) is the name of the most active form of vitamin E in humans. It is also a powerful biological antioxidant. Vitamin E in supplements is usually sold as alpha-tocopherol acetate, a form that protects its ability to function as an antioxidant. Alpha-tocopherol is a form of vitamin E that is easily converted by the body to vitamin E.

Antioxidants such as vitamin E act to protect cells against the effects of free radicals, which are potentially damaging by-products of energy metabolism. Free radicals can damage cells and may contribute to the development of cardiovascular disease and cancer. Studies are underway to determine whether vitamin E, through its ability to limit production of free radicals, might help prevent immune function, DNA repair, and other metabolic processes.

Recommendations for vitamin E are provided in the DRI. The RDA recommends the average daily dietary intake level that is sufficient to meet the nutrient requirements of nearly all (97-98%) healthy individuals in each age and gender group. An AI is set when there is insufficient scientific data available to establish an RDA. AIs meet or exceed the amount needed to maintain a nutritional state of adequacy in nearly all members of a specific age and gender group. The UL, on the other hand, is the maximum daily intake unlikely to result in adverse health effects.

In Table 3, below, RDAs for vitamin E are listed as alpha-tocopherol equivalents (ATE) to account for the different biological activities of the various forms of vitamin E. The table also lists RDAs for vitamin E in International Units (IU) because food and some supplement labels list vitamin E content in IUs (1 mg ATE vitamin E=1.5 IU). The upper tolerable limit for vitamin E has been established at 1500 IU daily.

TABLE 3

Recommended Dietary Allowances (RDAs) for Vitamin E.

| Age (Years) | Children (µg RAE) | Males (µg RAE) | Females (µg RAE) | Pregnancy (µg RAE) | Lactation (µg RAE) |
|---|---|---|---|---|---|
| 1-3 | 6 mg (9 IU) | | | | |
| 4-8 | 7 mg (10.5 IU) | | | | |
| 9-13 | | 11 mg (16.5 IU) | 11 mg (16.5 IU) | 15 mg (22.5 IU) | 19 mg (28.5 IU) |
| 14-18 | | 15 mg (22.5 IU) | 15 mg (22.5 IU) | 15 mg (22.5 IU) | 19 mg (28.5 IU) |

The term "vitamin E" is intended to include all functionally equivalent forms of tocopherol, however, d-alpha-tocopherol, d,l-alpha-tocopherol, and/or their esters including acetates and succinates (particularly the acetate form) generally can be used as a source of vitamin E. Other sources of vitamin E include beta-tocopherol, gamma-tocopherol, the tocotrienols, and their esters, tocopheryl nicotinate, polymeric tocopherol, and the like.

Vitamin C

In one embodiment of the composition of the present invention the dietary supplement comprises a daily dose of from about 400 mg to about 2000 mg of vitamin C (as ascorbic acid). In a preferred embodiment, the dietary supplement of the invention comprises from about 500 mg to about 1000 mg of vitamin C. In the most preferred embodiment, the invention comprises about 526 mg of vitamin C. This amount is designed to maximize the clinical effectiveness, bioavailability, and potency synergies in and among the other components of the present invention while still providing a comfortable safety margin to achieve vision stabilization and enhancement.

As used herein, the term "vitamin C" is intended to include all forms of vitamin C such as L-ascorbic acid, D-ascorbic acid, D,L-ascorbic acid, D-araboascorbic acid, dehydroascorbic acid, esters of ascorbic acid or their salts, and the like.

Vitamin C is a water-soluble, antioxidant vitamin. It is important in forming collagen, a protein that gives structure to bones, cartilage, muscle, and blood vessels. Vitamin C also aids in the absorption of iron, and helps maintain capillaries, bones, and teeth. As a water-soluble antioxidant, vitamin C is in a unique position to "scavenge" aqueous peroxyl radicals before these destructive substances have a chance to damage the lipids. Vitamin C also works with vitamin E to stop free radical chain reactions. Vitamin C lowers blood pressure and cholesterol levels, helps thin the blood and protect it against oxidation and works synergistically with vitamin E. Vitamin C also helps prevent atherosclerosis by strengthening the artery walls through its participation in the synthesis of collagen, and by preventing the undesirable adhesion of white blood cells to damaged arteries. An adequate intake of the vitamin is highly protective against stroke and heart attack.

A "good source" of vitamin C contains a substantial amount of vitamin C in relation to its calorie content and contributes at least 10% of the AI for vitamin C in a selected serving size. The AI for vitamin C is 90 mg per day for men and 75 mg per day for women (ages 19-50). The AI is also increased for smokers. Smoking increases oxidative stress—as a result, it is recommended that smokers consume 35 more mgs of vitamin C per day.

TABLE 4

Recommended Dietary Allowances (RDAs) for Vitamin C.

| Age (Years) | Children (μg RAE) | Males (μg RAE) | Females (μg RAE) | Pregnancy (μg RAE) | Lactation (μg RAE) |
|---|---|---|---|---|---|
| 1-3 | 40 mg | | | | |
| 4-8 | 45 mg | | | | |
| 9-13 | | 45-50 mg | 65-75 mg | | |
| 14-18 | | 75-90 mg | 65-75 mg | 90-95 mg | 90-95 mg |

Many experts are now realizing that the RDA of 60 mg/day is far too low to provide for optimum health and protection against disease. A team of medical researchers at the National Institutes of Health recently completed a study designed to determine the vitamin C requirements of healthy, young men. They found that a minimum intake of 1000 mg/day was required to completely saturate the blood plasma with vitamin C. They also found that vitamin C should be taken in divided doses throughout the day as urinary excretion increases rapidly when individual doses exceed 500 mg. The researchers concluded that the RDA should be raised to 200 mg/day. This amount of vitamin C can be obtained from a diet containing five daily servings of fresh fruit and vegetables. Unfortunately, less than 15% of children and adults in the US actually consume such a diet.

While 200 mg/day of vitamin C may be sufficient to maintain a reasonable health status in healthy, young men, it is clear that such a relatively low intake is far from adequate for older and sick people. It is also evident that far greater amounts are required to provide optimum protection against degenerative diseases such as heart disease.

It has long been accepted that a diet rich in vitamin C from fruits and vegetables provides protection against cancer and heart disease. However, very little evidence has been available as to whether that supplementation with vitamin C can increase this protective effect. This, however, is now changing. Researchers from the National Institute on Aging report that elderly people who take vitamin C and E supplements have a 50% lower risk of dying prematurely from disease than do people who do not supplement. A Californian study concluded that people who consume more than 750 mg/day of vitamin C reduce their risk of dying prematurely by 60%. Italian researchers have concluded that older people, especially the sick are exposed to a much higher level of oxidative stress than are younger people and that their low blood levels of vitamin C reflect this. Other researchers have found that people who suffer from asthma, arthritis, cancer, diabetes, and heart disease have much lower levels of vitamin C in their blood than do healthy people.

Large doses (1-2 g/day) of vitamin C have been found to reduce asthma symptoms significantly. Recent studies have shown that vitamin C concentrations in the blood from rheumatoid arthritis patients are extremely low and that vitamin C may protect against further damage to inflamed joints. Numerous studies have shown that an adequate intake of vitamin C is effective in lowering the risk of developing cancers of the breast, cervix, colon, rectum, esophagus, larynx, lung, mouth, prostate, and stomach.

Daily supplementation with 500 mg vitamin C for 10 years of more has been found to cut the risk of developing bladder cancer by 60%. The spread of breast cancer (metastasis) is now believed to be predominantly due to free radical damage which can be controlled through intake of increased amounts of vitamin C. Supplementation with 3 g/day of vitamin C has been found to effectively prevent further polyp growth in colon cancer and a vitamin C intake of more than 157 mg/day has been found to reduce the risk of developing colon cancer by 50%.

A recent study shows that people who supplement with more than 700 mg/day of vitamin C have a 62% lower risk of dying from hear disease than do people with a daily intake of 60 mg/day or less. Supplementation with 2 g/day of vitamin C has been found to reduce adhesion of monocytes to the lining of blood vessels and thereby reduce the risk of atherosclerosis. Vitamin C supplementation (2 g/day) also effectively reverses the vasomotor dysfunction often found in patients with atherosclerosis. Some very recent research carried out in Japan has shown that restenosis (reclosing of opened arteries) after angioplasty can be significantly reduced by supplementing with ascorbic acid (500 mg/day). Supplementing with vitamin C has been found to significantly lower the risk of cataracts and glaucoma and some very recent work has shown that open angle glaucoma can be reversed by supplementing with large doses of vitamin C.

The current RDA of 60 mg/day is clearly far too low and the proposed new RDA of 200 mg/day, while perhaps adequate for healthy, young males, would seem to be quite inadequate for older people and certainly too low for sick people. As a matter of fact, a scientific advisory panel to the U.S. Government sponsored Alliance for Aging Research recently recommended that all healthy adults increases their vitamin C intake to 250-1000 mg/day. A daily intake of 250-1000 mg of vitamin C may be adequate for preventive purposes, but far larger quantities are required in halting or reversing cancer and heart disease. Although there has been some concern that people suffering from hemochromatosis (a tendency to iron overload) may be sensitive to high doses of vitamin C, most researchers now agree that vitamin C is entirely safe even in daily quantities of 10 g or more.

Zinc

In one embodiment of the composition of the present invention the dietary supplement comprises a daily dose of from about 50 mg to about 200 mg of zinc (as zinc ascorbate 20%). In a preferred embodiment, the dietary supplement of the invention comprises from about 70 mg to about 100 mg of zinc. In the most preferred embodiment, the invention comprises about 80 mg of zinc. This amount is designed to maximize the clinical effectiveness, bioavailability, and potency synergies in and among the other components of the invention.

The body needs zinc for normal growth and health. For patients who are unable to get enough zinc in their regular diet or who have a need for more zinc, zinc supplements may be necessary. They are generally taken by mouth but some patients may have to receive them by injection. Lack of zinc may lead to poor night vision and wound-healing, a decrease in sense of taste and smell, a reduced ability to fight infections, and poor development of reproductive organs. Zinc compounds have anti-inflammatory and anti-infective properties. The beneficial properties of Zinc are discussed in Petrus E J et al., *Current Therapeutic Research*, 1998; 59(9): 595-607, which is incorporated herein by reference in its entirety.

Zinc is an essential trace element in human biology that is known to be necessary for many biological functions, such as growth, appetite, testicular maturation, skin integrity, mental activity, wound healing, and immune system maintenance. Approximately 300 enzymes are known to require zinc for their activities. Zinc deficiency in humans is widespread and is more prevalent in areas where the population subsists on cereal proteins.

Zinc compounds are acknowledged as anti-inflammatory agents, as astringents and beneficial in wound healing, and have antimicrobial, antifungal and antiviral activity. Zinc is the active agent in formulations to treat skin disorders, decubitus ulcers, abrasions, and has a tightening effect on sagging or loose skin. Zinc stabilizes the cell membranes and inhibits the formation of free radicals. Zinc also strengthens the integrity of blood vessel walls by reducing the membrane permeability and stopping bleeding. Unlike other metals, zinc is virtually nontoxic.

Zinc supplements have been used as a treatment for AMD. A growing body of evidence indicates that macular degeneration is driven by light-induced oxidizing damage suggesting that antioxidant enzyme systems could be important in slowing the progress of this disease. Tow enzymes, superoxide dismutase and catalase share zinc as a common cofactor. In addition to the AREDS study as discussed herein, a study published in 1988 concluded that zinc supplements were effective in the treatment of AMD, and that the zinc group remained stable and showed less accumulation of drusen.

The retina is susceptible to oxidative damage and that retinal damage can be modulated by the presence of antioxidant nutrients and zinc. Zinc may play a role in oxidant defense as a cofactor required for the activity of the enzymes. Zinc plays a role in numerous biochemical systems outside of oxidant defense that might also influence retinal integrity. Zinc is also a very potent inhibitor of nitric oxide synthase (NOS).

TABLE 5

US RDA Daily Recommended Intake for Zinc.

| Age | Amount (mg) |
| --- | --- |
| Infant to 3 years old | 5-10 |
| 4-6 | 10 |
| 7-10 | 10 |
| Adolescent and adult males | 15 |
| Adolescent and adult females | 12 |

Copper

In one embodiment of the composition of the present invention the dietary supplement comprises a daily dose of from about 1 mg to about 4 mg of copper (as copper gluconate). In a preferred embodiment, the dietary supplement of the invention comprises from about 1.5 mg to about 3.5 mg of copper. In the most preferred embodiment, the invention comprises about 2 mg of copper. This amount is designed to maximize the clinical effectiveness, bioavailability, and potency synergies in and among the other components of the invention.

The body needs copper for normal growth and health. For patients who are unable to get enough copper in their regular diet or who have a need for more copper, copper supplementation in the form of oral or injectable copper compounds may be necessary. Copper is needed to help the body use iron. It is also important for nerve function, bone growth, and to assist in carbohydrate metabolism. A lack of copper may lead to anemia and osteoporosis.

Copper is found in a variety of foods, including organ meats (especially liver), seafood, beans, nuts, and wholegrains. Additional copper can come from drinking water from copper pipes, using copper cookware, and eating farm products sprayed with copper-containing chemicals. Copper may be decreased in foods that have high acid content and are stored in tin cans for a long time. There is no RDA for copper, however, the normal daily recommended intakes are generally defined as in Table 6.

TABLE 6

Daily Recommended Intake for Copper.

| Age | Amount (mg) |
| --- | --- |
| Infant to 3 years old | 0.4-1 |
| 4-6 | 1-1.5 |
| 7-10 | 1-2 |
| Adolescent and adult males | 1.5-2.5 |
| Adolescent and adult females | 1.5-3 |

Selenium

In one embodiment of the composition of the present invention the dietary supplement comprises a daily dose of from about 50 µg to about 150 µg of selenium (as selenium amino acid chelate 0.2%). In a preferred embodiment, the dietary supplement of the invention comprises from about 60 µg to about 100 µg of selenium. In the most preferred embodiment, the invention comprises about 70 µg of selenium. This amount is designed to maximize the clinical effectiveness, bioavailability, and potency synergies in and among the other components of the invention.

Selenium is a trace mineral that is essential to good health but required only in small amounts. Selenium is incorporated into proteins to make selenoproteins, which are important antioxidant enzymes. The antioxidant properties of selenoproteins help prevent cellular damage from free radicals. Free radicals are natural by-products of oxygen metabolism that may contribute to the development of chronic diseases such as cancer and heart disease. Other selenoproteins help regulate thyroid function and play a role in the immune system.

Plant foods are the major dietary sources of selenium in most countries throughout the world. The content of selenium in food depends on the selenium content of the soil where the plants are grown or animals are raised. For example, researchers know that soils in the high plains of northern Nebraska and the Dakotas have very high levels of selenium. People living in those regions generally have the highest selenium intakes in the United States. In the U.S., food distribution patterns across the country help prevent people living in low-selenium geographic areas from having low dietary selenium intakes. Soils in some parts of China and Russia have very low amounts of selenium. Selenium deficiency is often reported in those regions because most food in those areas is grown and eaten locally.

The Institute of Medicine of the National Academy of Sciences has set a tolerable upper intake level (UL) for selenium at 400 μg/day for adults to prevent the risk of developing selenosis.

TABLE 7

USRDA Daily Recommended Intake for Selenium.

| Age | Males/Females (μg) | Pregnancy (μg) | Lactation (μg) | UL (μg) |
|---|---|---|---|---|
| Infant to 3 years old | 20 | — | — | 90 |
| 4-8 | 30 | — | — | 150 |
| 9-13 | 40 | — | — | 280 |
| 14-18 | 55 | 60 | 70 | 400 |
| 19+ | 55 | 60 | 70 | 400 |

The above-mentioned minerals in the composition of the invention are typically in salt form. Such salts can be any of the well known salts including, for example, carbonate, oxide, hydroxide, chloride, sulfate, phosphate, gluconate, lactate, acetate, fumarate, citrate, malate, amino acids, and the like for the cationic minerals and sodium, potassium, calcium, magnesium, and the like for anionic minerals. The particular salts used and their levels selected in the embodiments of the invention were chosen to minimize their interaction with other supplement ingredients in the composition.

Lutein

In one embodiment of the composition of the present invention the dietary supplement comprises a daily dose of from about 10 mg to about 20 mg of lutein (as 5% FloraGLO®). In a preferred embodiment, the dietary supplement of the invention comprises from about 12 mg to about 18 mg of lutein. In the most preferred embodiment, the invention comprises about 15 mg of lutein. This amount is designed to maximize the clinical effectiveness, bioavailability, and potency synergies in and among the other components of the invention.

Lutein is a carotenoid—a pigment compound—found in green leafy vegetables, eggs, corn, and carrots. Lutein is an antioxidant that helps to reduce harmful free radicals that can occur in cells and may contribute to cell damage. Lutein also filters or absorbs cell-damaging, high-energy blue light from the visible light spectrum. Lutein also acts as an antioxidant, protecting cells against the damaging effects of free radicals. These protective qualities enable lutein to protect plant cells from sunlight and oxidative stress. The same qualities also protect human cells in the retina of the eye, the skin, and other organs and tissues from these same damaging factors.

With these unique attributes in mind, more than 300 peer-reviewed studies have connected lutein with benefits in eye, skin, and heart, as well as in different types of cancer, immune diseases, and diabetes. In particular, lutein has been associated with reducing the risk of age-related macular degeneration, the leading cause of vision loss among older Americans.

Lutein is found naturally in the body but lutein is not manufactured by the body. Instead, lutein must be obtained from food or dietary supplements. Studies indicate that the average American ingests one to two mg of lutein daily. Nutrition experts currently use 6 mg a day as a suggested guideline but science also suggests consuming at least 12 mg of lutein daily to protect both the eyes and the skin. Lutein can be converted to zeaxanthin in the blood serum and is the key carotenoid for providing the proper amount of lutein and zeaxanthin in the retina. One study demonstrated that a diet of 6 mg of lutein per day led to a 43% lower prevalence of AMD. Lutein and zeaxanthin work by accumulating in the macula. There are no known toxicity or overdose concerns regarding lutein consumption. Extremely high consumption of lutein may result in the skin taking on an orange or yellow color, known as carotenodermia. This occurrence is thought to be harmless.

In an overview of research on carotenoids, the Roche company concluded that lutein and zeaxanthin possess physical and chemical properties that make them biologically well suited to protect the macula and lens. In addition, they concluded that based on typical intake in the general population, and the recommended intake amounts of lutein and zeaxanthin associated with reduced disease risk; most individuals may need to increase consumption of these carotenoids to cover a potential dietary gap of at least 2-4 mg/day.

Zeaxanthin

In one embodiment of the composition of the present invention the dietary supplement comprises a daily dose of from about 0.5 mg to about 4 mg of zeaxanthin (as 5%). In a preferred embodiment, the dietary supplement of the invention comprises from about 1 mg to about 3 mg of zeaxanthin. In the most preferred embodiment, the invention comprises about 1 mg of Zeaxanthin [from Roche] or as an herbal extract, for example, marigold extract. This amount is designed to maximize the clinical effectiveness, bioavailability and potency synergies in and among the other components of the invention.

Progress is being made in the study of both lutein and zeaxanthin as potentially effective dietary supplements for macular degeneration patients. According to a 1995 study, increasing the consumption of dark green, leafy vegetables appears to offer some protection against macular degeneration. Because nutritional factors may play a role in AMD, researchers decided to correlate the disease with dietary antioxidant intake in subjects participating in the NIH Eye Disease Case-Control Study. The investigators found that higher intakes of carotenoids were associated with a reduced risk of wet macular degeneration. The carotenoids lutein and zeaxanthin were the most strongly associated with a reduced risk of macular degeneration. These are obtained primarily from dark green, leafy vegetables such as spinach, collard greens, kale, mustard greens, and turnip greens. Eating spinach and collar greens five or more times a week was found to noticeably reduce the risk of macular degeneration. Other conclusions from the study included: the intake of retinol supplements had no effect on AMD; vitamin C from food intake had little effect; vitamin E, in high doses, actually showed negative effects.

In addition to functioning as antioxidants, lutein and zeaxanthin may help to protect the retina by additional mechanisms. For example, lutein and zeaxanthin may protect the retina against photodamage by filtering out the blue light, which is not stopped by the cornea and lens, and which can damage the retina over time. In addition, these nutrients may protect against the peroxidation of fatty acids and lipids in the photoreceptor membrane. Finally, evidence indicates that lutein and zeaxanthin also protect the blood vessels that supply the macular region.

Bilberry Extract

In one embodiment of the composition of the present invention the dietary supplement comprises a daily dose of from about 50 mg to about 120 mg of bilberry extract (as 4:1 fruit). In a preferred embodiment, the dietary supplement of the invention comprises from about 55 mg to about 100 mg of bilberry extract. In the most preferred embodiment, the invention comprises about 60 mg of bilberry extract. This amount is designed to maximize the clinical effectiveness, bioavailability, and potency synergies in and among the other components of the invention.

Bilberry (Vaccinium myrtillus) is a short, shrubby perennial plant that inhabits the woods and forest meadows of Europe, Western Asia, and the Rocky Mountains of North America. As with many other plants that below to the same plant family (Vaccinium), bilberry bears edible fruits similar to those found on the American blueberry bush. Cranberries and huckleberry belong to this plant family, too.

The bilberry is a bluish-black berry, which is creamy white inside. It has been valued as a food since prehistoric times. Commonly referred to as "European blueberry," it is framed as a filling for pies, and for use in cobblers, jams, and other recipes. In addition, for at least one thousand years, European herbalists have also recommended the plant's fruit s and leaves for medicinal purposes, treating a variety of complaints with a strong, boiled tea made from the plant. Urinary tract infections, kidney stones, and diarrhea are just a few of the ailments for which bilberry has been used.

Bilberry's modern reputation as a healing plant was sparked during World War II when British Royal Air Force (RAF) pilots noticed that their night vision was sharper than usual whenever they ate bilberry preserves before starting out on their evening bombing raids. Subsequent research revealed that bilberries are powerful antioxidants, capable of protecting cells in the eye and other parts of the body against damage from unstable oxygen free radicals. Researchers intrigued by the improved night vision of the bilberry-eating RAF pilots eventually identified compounds in the berry called anthocyanosides. These substances appear to fortify blood vessel walls, improving blood flow to the tiny blood vessels that keep eyes healthy, as well as to larger blood vessels that help maintain good circulation throughout the body. Anthocyanosides also appear to strengthen collagen, the protein that provides support to healthy connective tissue.

The other important healing substance in bilberry fruits, astringent compounds called tannins, help treat such ailments such as diarrhea, sore throat, and inflammation. German health authorities approve bilberry fruit for mild cases of diarrhea and mouth and throat inflammation. A cooled tea made from dried berries can be either drunk or gargled for these purposes. Today, bilberry ranks among the most popular of supplements for maintaining healthy vision and for treating various vision disorders, including poor night vision, and cataracts.

In addition to improving night vision, bilberry may be useful for the prevention of macular degeneration, cataracts (a clouding in the eye's lens that is common in older people), and venous insufficiency. In one study of 50 patients with age-related cataracts, it was found that taking bilberry extract along with vitamin E supplements stopped the progression of cataracts in nearly all of the participants. It remains unclear, however, whether the vitamin, the bilberry or even the combination of the two was responsible for this beneficial effect. In addition, the active ingredients in bilberry appear to enhance blood flow to vessels that circulate blood throughout the body. For this reason, the herb may benefit people suffering from poor circulation in their extremities, painful varicose veins, and hemorrhoids—all discomforts that can be expected to improve with enhanced circulation.

High-quality, pharmaceutical-grade bilberry (as is used in the present invention) is made into potent extracts from whole, dried, ripe fruit. The extracts of anthocyanidins are then standardized to contain 23% to 37% bilberry bioflavanoid complex anthocyanosides for greatest efficacy.

There is no known drug or nutrient interactions associated with bilberry. Bilberry fruit extract has no known side effects when taken at recommended dose, even when used on a long term basis.

Eyebright

In one embodiment of the composition of the present invention the dietary supplement comprises a daily dose of from about 60 mg to about 250 mg of Eyebright (as herb powder). In a preferred embodiment, the dietary supplement of the invention comprises from about 100 mg to about 200 mg of Eyebright. In the most preferred embodiment, the invention comprises about 120 mg of Eyebright. This amount is designed to maximize the clinical effectiveness, bioavailability, and potency synergies in and among the other components of the invention.

Eyebright is a small plant, 2 to 8 inches high, an annual, common on heaths and other dry pastures, especially on a chalky soil, and flowering from July to September, with deeply-cut leaves and numerous, small, white or purplish flowers variegated with yellow. Eyebright leaf has long been recognized for its eyesight enhancing properties. Eyebright has been used primarily for the management of eye fatigue and to promote vision. Herbalists also use eyebright for respiratory tract concerns, including sinus and throat support.

Spinach

In one embodiment of the composition of the present invention the dietary supplement comprises a daily dose of from about 30 mg to about 100 mg of spinach (as spinach leaf powder). In a preferred embodiment, the dietary supplement of the invention comprises from about 40 mg to about 80 mg of spinach. In the most preferred embodiment, the invention comprises about 70 mg of spinach. This amount is designed to maximize the clinical effectiveness, bioavailability, and potency synergies in and among the other components of the invention.

Alfalfa

In one embodiment of the composition of the present invention the dietary supplement comprises a daily dose of from about 20 mg to about 80 mg of alfalfa (as alfalfa grass powder). In a preferred embodiment, the dietary supplement of the invention comprises from about 30 mg to about 60 mg of alfalfa. In the most preferred embodiment, the invention comprises about 40 mg of alfalfa. This amount is designed to maximize the clinical effectiveness, bioavailability, and potency synergies in and among the other components of the invention.

Alfalfa is a very mild, food-like medicinal plant. Since it is do mild, it is well tolerated by a wide variety of people, and has many uses. Alfalfa is a rich natural source of supplemental minerals and vitamins. Since alfalfa is a legume, it is rich in phytoestrogens, notably isoflavones, which have become popular for their positive effects on hormonal actions in the body.

Alpha-Lipoic Acid (ALA)

In one embodiment of the composition of the present invention the dietary supplement comprises a daily dose of from about 0.001 mg to about 100 mg ALA. In a preferred embodiment, the dietary supplement of the invention comprises from about 0.005 mg to about 60 mg of ALA. In the most preferred embodiment, the invention comprises about 0.005 mg of ALA. This homeopathic amount is designed to maximize the clinical effectiveness, bioavailability, and potency synergies in and among the other components of the invention.

ALA is a potent antioxidant and anti-inflammatory agent that is both water and fat soluble making it the universal antioxidant. It is the only antioxidant that protects both the water and lipid parts of the cell. The present invention uses ALA as an anti-inflammatory agent because of its effects within the cell.

Alpha-lipoic acid works together with other antioxidants such as vitamins C and E. It is important for growth, helps to prevent cell damage, and helps the body rid itself of harmful substances. Good food sources of alpha-lipoic acid include spinach, broccoli, beef, yeast (particularly Brewer's yeast), and certain organ meats (such as the kidney and heart). Currently there are no established recommended doses for supplementation. For general antioxidant support, the recommended dose of ALA is 20 mg to 50 mg per day. Because alpha-lipoic acid has been associated with improved blood sugar control, people with diabetes should follow their blood sugar levels carefully when taking this supplement in order to avoid hypoglycemia (low blood sugar).

ALA is may be contraindicated for patients taking certain medications. For example, In an animal study, alpha-lipoic acid supplements reduced side effects, particularly toxicity to the ear, associated with amikacin, and gentamicin. The use of alpha-lipoic acid supplements in animals protected against toxic side effects associated with cisplatin and cyclophosphamide. In addition, rats given alpha-lipoic acid supplements had altered thyroid hormone function, but improved cholesterol levels. Blood hormone levels and thyroid function tests should be monitored closely in people taking thyroid hormones who are also taking alpha-lipoic acid.

Citrus Bioflavanoid Complex (CBC)

In one embodiment of the composition of the present invention the dietary supplement comprises a daily dose of from about 10 mg to about 50 mg CBC (35%). In a preferred embodiment, the dietary supplement of the invention comprises from about 15 mg to about 45 mg of CBC. In the most preferred embodiment, the invention comprises about 18 mg of CBC. This amount is designed to maximize the clinical effectiveness, bioavailability, and potency synergies in and among the other components of the invention.

Flavonoids or bioflavonoids are widely distributed in plants fulfilling many functions including producing yellow or red/blue pigmentation in flowers and protection from attack by microbes and insects. The widespread distribution of flavonoids, their variety and their relatively low toxicity compared to other active plant compounds mean that many animals, including humans, ingest significant quantities in their diet. Flavonoids have been referred to as "nature's biological response modifiers" because of strong experimental evidence of their ability to modify the body's reaction to allergens, viruses, and carcinogens. They show anti-allergic, anti-inflammatory, anti-microbial and anti-cancer activity. In addition, flavonoids act as powerful antioxidants, protecting against oxidative and free radical damage.

CBC contains a variety of bioflavanoids including flavonones, for example, hesperidins, naringenin, and eriodictyol; flavonols, for example, quercetin, rutin, kaempferol, myricetin, and isorhamnetin; and flavones, for example, luteolin, apigenin.

Inert Matrix

The inert matrix of the present invention comprises at least one of the following: cellulose fiber (as BH 200), magnesium (as magnesium stearate), and silica. In certain embodiments, the composition of the invention comprises from about 60 mg to about 100 mg of cellulose fiber. In a preferred embodiment the composition of the invention comprises about 80 mg of cellulose fiber. In other embodiments, the composition of the invention comprises from about 10 mg to about 40 mg of magnesium. In a preferred embodiment, the invention comprises about 20 mg of magnesium. In still other embodiments, the composition of the invention comprises from about 15 mg to about 35 mg of silica. In a preferred embodiment, the composition of the invention comprises about 28 mg of silica. In one of the preferred embodiments, the amount of inert matrix is from about 10% and about 50% by weight. In another of the preferred embodiments, the invention comprises about 120 mg (or 20% by weight) of inert matrix per dosage unit. This amount is designed to maximize the clinical effectiveness, bioavailability, and potency synergies in and among the other components of the invention.

In any of the embodiments described herein, the composition may further comprise a pharmaceutically acceptable excipient or carrier component, for example, lactose, glucose, sucrose, corn starch, potato starch, and cellulose esters such as cellulose acetate, ethyl cellulose, calcium silicate, talc, fatty acids, such as stearic acid, microcrystalline cellulose, carnauba wax, and the like or combinations thereof. In addition, in any of the embodiments the composition of the invention may further comprise a diluent, or other additive, such as binders, fillers, supports, thickening agents, flavoring agents, gums, coloring agents, preservatives, stabilizers, regulators, emulsifiers, flow agents, absorbents, and the like or combinations thereof. In still another embodiment, the composition of the invention may comprise a dietary fiber supplement, for example oat bran or other natural fiber source. The present invention includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985) hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose or effective amount, is that dose required to prevent, inhibit the occurrence of, or treat (alleviate a symptom to some extent, preferably all of the symptoms) a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize.

It is contemplated that the composition of the invention can be in any pharmaceutically acceptable form suitable for administration to an individual. For example, in any of the preferred embodiments, the composition can be in the form of a powder, a solid, a gel, a liquid, an emulsion, cream, capsule, tablet, gel capsule, liquid filled capsule, time release capsule or tablet (e.g., quick release, extended release or combination thereof), enterically coated tablet (e.g., controlled release), and the like or combinations thereof. The composition of the invention and formulations thereof can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising the dietary supplement of the invention and a pharmaceutically acceptable carrier. The composition of the invention can be present in association with one or more non-toxic pharmaceutically acceptable carriers and/or diluents and/or adjuvants, and if desired other active ingredients. The composition of the invention can be in a form suitable for oral use, for example, as tablets, troches, lozenges, aqueous or oily suspensions, dispersible powders or granules, topical eyedrops, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or acetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono-or diglycerides. In addition, fatty acids such as oleic acid find use in the preparation of injectables.

The composition of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

The composition of the invention can be administered parenterally in a sterile medium. The supplement, depending on the vehicle and concentration used, can either be suspended or dissolved in the vehicle. Advantageously, adjuvants such as local anesthetics, preservatives and buffering agents can be dissolved in the vehicle. The amount of active ingredient that can be combined with the carrier materials to produce a single dosage form varies depending upon the host treated and the particular mode of administration. Dosage unit forms generally contain between from about 1 mg to about 1 g of an active ingredient(s). It is understood that the specific dose level for any particular patient or subject depends upon a variety of factors including the activity of the specific compound employed, the age, body weight, general health, sex, diet, time of administration, route of administration, and rate of excretion, combination of active species, and the severity of the particular disease undergoing therapy.

Although the invention has been described primarily in combination with special and preferred embodiments, it will be understood that it is capable of modification without departing from the overall scope of the invention. As such, the claims are intended to cover all variations, uses, or adaptations of the invention, which would be apparent to one of ordinary skill in the art from the present teachings. Additional advantageous features and functionalities associated with the systems, methods and processes of the present invention will be apparent from the examples which follow.

EXAMPLE #1

Compounding Method and Formulation

In another aspect, the present invention relates to method for compounding the dietary supplement of the invention. In addition to other factors, selecting the proper compounding method of the dietary supplement is essential to the ultimate potency, bioavailability, and clinical efficacy of the final composition. Even slight variations among any of the factors involved can potentially decrease the potency of one or more components thus modifying the clinical efficacy of the dietary supplement. Factors considered during the compounding method include, for example, the raw material selection and quantity, batching order, processing, mixing, compounding, timing, room conditions.

In an embodiment, the dietary supplement of the present invention is produced in batches. In certain embodiments, a batch is designed to produce 5,000 bottles of 120 capsules each (with a 10% overage allowance for testing and in-process analysis). In a preferred embodiment, the method of the invention comprises the steps of blending the formulation in a blender for from about 10 minutes to about 1 hour, at a temperature of from about 5° C. to about 50° C., and relative humidity of from about 20% to about 75%. In another of the preferred embodiments, the invention relates to a method for compounding a dietary supplement composition comprising the steps of providing a suitable amount of the dietary supplement of the invention; blending the formulation in a blender for about 20 minutes, at a temperature of about 25° C., and at 50% humidity.

Prior to each batch run, all of the following steps are completed in each of the staging room, mixing room, and quarantine room prior to initiating the run since time is of the essence to assure tight control over environmental exposures to the in-process mix. In order to maximize consistency, each batch of the present invention is completed as a single run as opposed to a sequence of serial or parallel premixing steps.

Each batch is assigned a lot number which is recording according to cGMP directives. The staging room is cleaned thoroughly to industry standards and is so logged. The correct bulk raw materials are isolated from any other raw materials that may be on site and are brought into the staging room and checked for correctness. The bulk raw materials are then released by the quality control manager (QCM) for processing. All required utensils and the appropriate number and size poly-ethylene lined drums are then selected for the batch run. Each drum is prepared, cleaned, inspected, and labeled for its respective component. In the weight room, all balances are calibrated to manufacturer's tolerances. In the mixing room, the final balances and the blender apparatus is thoroughly cleaned and inspected according to the manufacturers' specifications and cGMP regulations and is logged as clean. All prior labels or other identifiers are removed and discarded.

Once all of the rooms are made ready as above, each component container, one at a time, is brought into the weight room along with its corresponding bulk raw material. Each empty component container is weighed and labeled with the empty tarred weight. The final desired tarred weight of the container with its respective raw material is then calculated, labeled and documented. One at a time, each raw material component is removed from its respective bulk package and is sifted with the appropriate screens into its respective labeled container located on the balance and filled to the appropriate amount (weight), including overage, sealed and set aside. The process is continued until all components are readied for mixing.

In the mixing room, the blender is identified with the correct batch number and product code name and documented according to cGMP guidelines. The containers with the sifted raw materials are then lined up in order. Each component is then removed from its respective sealed drum, tarred on the calibrated scales, and added to the blender which is running at slow speed. Table 8 indicates one embodiment of the method of the invention, the ingredients are added batch-wise in the following order and in the following amounts:

TABLE 8

Example Batch Formulation of the Dietary Supplement of the Invention.

| Component | Weight (%) | Batch Amount (kg) |
| --- | --- | --- |
| Vitamin A (as retinyl Palmitate 250 IU/mg) | 0.44 | 1.65 |
| Beta-Carotene (as Betatene ™ 7.5%; 119 IU/mg) | 0.92 | 3.47 |
| Vitamin E (as d,l-alpha tocopherol acetate 750 IU/g) | 23.48 | 87.98 |
| Vitamin C (as ascorbic acid) | 23.17 | 86.84 |

TABLE 8-continued

Example Batch Formulation of the Dietary Supplement of the Invention.

| Component | Weight (%) | Batch Amount (kg) |
|---|---|---|
| Zinc (as zinc ascorbate 20%) | 17.61 | 66.00 |
| Copper (as copper gluconate USP 14%) | 0.63 | 2.357 |
| Selenium (as selenium amino acid chelate 0.2%) | 0.15 | 0.5775 |
| Lutein (as 5% FloraGLO ®) | 13.21 | 49.50 |
| Zeaxanthin | 0.13 | 0.495 |
| Bilberry Extract (as 4:1 fruit) | 2.64 | 9.90 |
| Eyebright (herb powder) | 5.28 | 19.80 |
| Spinach (leaf powder) | 3.06 | 11.547 |
| Alfalfa (grass powder) | 1.76 | 6.60 |
| Alpha-Lipoic Acid | 0.001 | 0.0033 |
| Citrus Bioflavanoid Complex (35%) | 2.20 | 8.25 |
| Inert Matrix (cellulose fiber; BH 200) | 3.52 | 13.20 |
| Magnesium (as magnesium stearate) | 0.88 | 3.30 |
| Silica (inert matrix) | 0.88 | 3.30 |
| TOTAL | 100% | 374.78 kg |

Once all materials are added into the turning blender; the composition is blended for about 20 minutes with the blender direction changed or reversed after 10 minutes. The contents are emptied into clean, labeled and tarred drums. Samples from each drum are randomly removed for qualitative and quantitative analysis. The drum is sealed and labeled "Quarantine" and placed into the quarantine room until the analysis are completed and the proper reports filed.

The percent yield is then calculated by the formula:

Gross Weight−Tare Weight=Total Net Weight    1.

The Total Net Weight is divided by the Theoretical Weight Factor, (in this equaling 374.77) to determine the percent yield by:

Total New Weight/Theoretical Weight Factor=Percent Yield    2.

Once all the analytical reports are reviewed and the components, compositions, and formulations are verified, the quarantined drums are ready to be relocated to the encapsulating room. The QCM marks the drums as cleared for encapsulating. The encapsulating room is thoroughly cleaned, with all labels and product identifiers removed and documented as per cGMP regulations. The blended material stored in the sealed drums is brought to the encapsulating room. The encapsulating process proceeds as per industry standard methods. The preferred embodiment uses "0" red/white capsules, although many other capsule possibilities exist. The theoretical weight of each capsule is 667.83 mg each. The capsule weight tolerances are set at 634.44 mg to 701.22 mg each. The blended material is removed from each sealed drum and introduced into the encapsulating equipment. Any and all residual blended material remaining in the drums is labeled as start-up waste and removed for disposal. As the encapsulation process is underway, every 20 minutes, ten capsules are removed and weighed to check tolerances. The capsules are discharged and polished and placed into new drums labeled "Quarantine" and moved into the quarantine room with the appropriate documents.

Once the final reports have been reviewed by the QCM, the drums with the capsules are moved to the packaging room. The packaging room has been cleaned and inspected and all prior labels and product identifiers have been removed according to all cGMP regulations. Although many possible combinations are possible, the preferred embodiment of the present invention utilizes 200 cc Setco white HDPE bottles to contain the 120 count capsules containing the preferred embodiment of the invention. A 45/400 mm white ribbed PS22 cap is used to close the bottle. A 77×23 SFYP seal is placed onto the bottle to seal it. The label is placed onto the bottle and 12 bottles are placed into labeled cases for shipping. The designated expiration is 3 years. Obviously, sample amounts may be packaged separately in small bottles, blister packs and other means well-known in the art.

The composition of the present invention can be in any pharmaceutically acceptable form, such as, tablets, caplets, gel tabs, capsules, liquid, and controlled or sustained release formulations, and the like. These dosage forms can be formulated, prepared, and packaged according to manufacturing techniques that are currently known or become known in the art.

The size of the tablet, capsule, or caplet is typically the limiting factor. If however, one or more vitamins, minerals, anti-oxidants, carotenoids, and/or other nutrients are to be incorporated along with the components of the preferred embodiment of the invention, the overall size of the tablet or caplet might be so large as to make swallowing difficult. This problem can be circumvented, for example, by dividing the concentration of each ingredient in half and increasing the dose to two or more tablets or caplets or the like per day. Since each caplet would be smaller in size, the divided dose would be easier to swallow.

Although patient compliance historically increases with decreasing dosing regimens, maximizing the bioavailability and distribution of the active ingredients may require frequent dosing. Thus in certain embodiments the invention comprises not less than one or more than six daily divided doses to deliver the composition of the invention. In a preferred embodiment, the invention comprises a daily dose of the dietary supplement of the invention divided into four capsules or tablets. In another embodiment the daily dose is divided into two capsules or tablets. In another of the preferred embodiments, the invention includes a method for orally administering an effective amount of the composition of the invention to an individual who has been diagnosed with the dry form of age-related macular degeneration.

EXAMPLE #2

Multicenter Investigation of Rheopheresis for AMD ("MIRA-1") Clinical Study

The MIRA-1 trial protocol involved a 12-month, prospective, double-blind, randomized, reference-controlled trial designed to test the safety and efficacy of an experimental double filtration apheresis technology for the treatment of select patients with the dry form of AMD. The study enrolled 183 intent-to-treat patients for which complete data sets were evaluated. The primary endpoint was the difference in the mean change in vision between the treatment and control groups at the 12 month post baseline interval.

Patients were randomized into two groups; 2:1 in favor of the experimental arm. Eligible patients had to have a diagnosis of D-AMD, baseline ETDRS (Early Treatment Diabetic Retinopathy Scale) LogMAR (log of the mean angle of resolution) BSCVA (best spectacle-corrected visual acuity) vision between 20/32 and 20/125, multiple large soft drusen morphology, elevated laboratory values of two out of three of IgA, fibrinogen or Total Cholesterol, among other factors.

In the second half of the study, 89 patients utilized the dietary composition of the invention over the 12-months of the study, comprising approximately 65,000 doses which consumed 130,000 capsules. The control or reference arm of the study was comprised of 36 intent-to-treat patients, who used a combination of sham apheresis treatment plus the composition of the invention. Thus the only active treatment being administered in the control arm of the study was the daily ingestion of the oral dietary supplement of the invention.

The sixty-three patients in the experimental arm of the second half of the MIRA-1 study used the composition of the invention in combination with an active treatment protocol of the apheresis technology.

Results. The study was enrolled in two enrollment periods. The composition of the invention was utilized in all patients in the second enrollment session. Both study groups (reference and experimental) demonstrated a mean improvement in overall LogMAR BSCVA. A documented mean improvement was achieved by the control arm where the only active treatment was the provision of the composition of the invention. A similar improvement was achieved by the experimental arm, which was also receiving the composition of the invention plus apheresis. The difference between the groups was not statistically significant. FIGS. 1-5 summarize the results of the control group of the MIRA-1 trial.

Age-Related Eye Disease Study ("AREDS")

The age-related eye disease study is a major clinical trial sponsored by the National Eye Institute, one of the Federal Governments National Institutes of Health and has been conducted over the past 15 years. The AREDS trial was designed to learn more about the natural history and risk factors of age-related macular degeneration (AMD) and cataract; and to evaluate the effect of high doses of antioxidants and zinc on the progression of AMD and cataract.

AREDS Results. In December 1999, the initial 7-year results were published from the AREDS trial which showed that taking oral preparations of high levels of antioxidants and zinc significantly reduce the risk of advanced age-related macular degeneration (AMD) and its associated vision loss. These same nutrients had no significant effect on the development or progression of cataract.

The AREDS study included two clinical trials—one for AMD and one for cataract—that generally shared one pool of participants. There were 4,757 participants, ages 55-80 years old, enrolled in the study. Because 1,117 participants did not have at least early stages of AMD, the AMD trial included only the 3,640 participants who had at least had early AMD. The cataract results are based on 4,629 enrollees; 128 of the 4,757 participants had cataract surgery on both eyes prior to enrollment and therefore were ineligible for the cataract clinical trial.

The participants' stages of disease ranged from no evidence of AMD in either eye, to advanced AMD with vision loss in one eye but good vision (at least 20/30) in the other eye. The participants were enrolled in 11 clinics nationwide. Fifty-six percent were female; the median age was 69 years. Enrollment began in November 1992 and ended in January 1998-some follow up continues to the present day. About 90% of all participants were followed for a minimum of five years; about 2% were lost to follow-up; about 1% had been in the study less than five years; and about 7% died before five years.

TABLE 9

AREDS Trial, Patient Categories.

| Category 1 | Category 2 | Category 3 | Category 4 |
|---|---|---|---|
| No AMD A few small or no drusen | Early Stage AMD Several small drusen or a few medium-sized drusen in one or both eyes | Intermediate AMD Many medium-sized drusen or one or more large drusen in one or both eyes | Advanced AMD In one eye only, either a bread-down of light-sensitive cells and supporting tissue in the central retinal area (advanced dry form) or abnormal and fragile blood vessels under the retina (wet form) |

Depending on their stages of AMD, the AREDS participants were placed in one of four categories. The one constant was that at least one eye of each participant had to be free from any vision-threatening eye disease other than AMD or cataract, and that eye could not have had previous surgery, except for cataract surgery. In Category One, participants had no AMD and a few small or no drusen in either eye. In Category Two, participants had early AMD either several small drusen or a few medium-sized drusen in one or both eyes. Category Three participants had intermediate AMD— either many medium-sized drusen or one or more large drusen in one or both eyes; these participants were at high risk for developing advanced AMD, which is generally defined as either a break-down of light-sensitive cells and supporting tissue in the central retinal area (advanced dry form), or abnormal and fragile blood vessels under the retina (wet form). Category Four participants already had advanced AMD in one eye, and in the other eye had good vision with no sign of advanced AMD. Previous studies had shown that the eye without AMD was at high risk for developing advanced AMD.

The participants in each category were randomly selected to receive daily oral tablets for one of four treatments: 1) zinc alone; 2) antioxidants alone; 3) a combination of antioxidants and zinc; or 4) a placebo, a harmless substance that looks like the real treatment but has non effect on eye disease. The antioxidant formulation contained a combination of vitamin C, vitamin E, zinc, copper, and beta-carotene. The specific daily amounts of antioxidants and zinc used by the AREDS researchers were 500 milligrams of vitamin C; 400 international units of vitamin E; 15 milligrams of beta-carotene; 80 milligrams of zinc as zinc oxide; and two milligrams of copper as cupric oxide. In the study's planning stages, a panel of nutritionists, opthalmologists, and biochemists reviewed the basic science and epidemiological data and recommended these vitamins and dosages.

TABLE 10

AREDS Trial Therapeutic Classes.

| Antioxidant Plus Zinc Alone | Zinc Alone | Antioxidants |
|---|---|---|
| Reduced risk of developing advanced AMD by about 25%. | Reduced risk of developing advanced AMD by about 21%. | Reduced risk of developing advanced AMD by about 17%. |

TABLE 10-continued

AREDS Trial Therapeutic Classes.

| Antioxidant Plus Zinc Alone | Zinc Alone | Antioxidants |
|---|---|---|
| Reduced risk of vision loss by about 19%. | Reduced risk of vision loss by about 11%. | Reduced risk of vision loss by about 10%. |

AREDS scientists found that people at high risk for developing advanced AMD —those with intermediate AMD, and those with advanced AMD in one eye only—reduced their risk of developing advanced stages of AMD by about 25% when treated with the combination of "antioxidants plus zinc." The combination of "antioxidants plus zinc" also reduced the risk for central vision loss by 19% in the same group. Participants at high risk for developing advanced AMD who were treated with "zinc alone" reduced their risk of developing advanced AMD by about 21% and their risk of vision loss by about 11%. Participants who were treated with "antioxidants alone" reduced their risk of developing advanced stages of AMD by about 17% and their risk of vision loss by about 10%.

The study was not designed to evaluate the effect of the antioxidants and zinc in the study participants who initially had no AMD (Category One). This is because previous studies had indicated that people aged 60 and over with no AMD have a very low risk for developing a clear progression of AMD within a seven-year period (the life of the AREDS clinical trial). The AREDS study confirmed this low risk—participants with no AMD had less than a 1% chance of losing vision from AMD during the study.

For those study participants who initially had early AMD (Category Two), the antioxidants and zinc used by the AREDS researchers did not slow the disease's progression to intermediate AMD. Consequently, there is no apparent need for those diagnosed with early AMD to take the combination studied in the AREDS.

Thus the overall results of the AREDS study demonstrated a slowing of disease progression as opposed to actual vision improvement. Thus the daily oral administration of 500 mg of vitamin C; 400 IU of vitamin E; 15 mg of beta-carotene; 80 mg of zinc; and 2 mg of copper as cupric oxide, slows progression but was unable to induce an enhancement or even a preservation of vision. This was true at each of the seven 12-month intervals for the seven year trial.

AREDS Formula Supplements. Subsequent to the publication of the AREDS trial, numerous companies have developed and commercialized neutraceuticals with various compositions based on the AREDS formulation. Products like Bausch and Lomb's PreserVision® AREDS and OccuVite® supplements, and others similarly formulated, are now considered the standard of care for patients with Category 3 and 4 dry AMD. Thus, there is very little differentiation in the marketplace for such similarly-formulated products. Consequently, the clinical results provided by each of these products are similar, with slowing of disease progression being the primary treatment objective and the most common result achieved.

Figure 6:
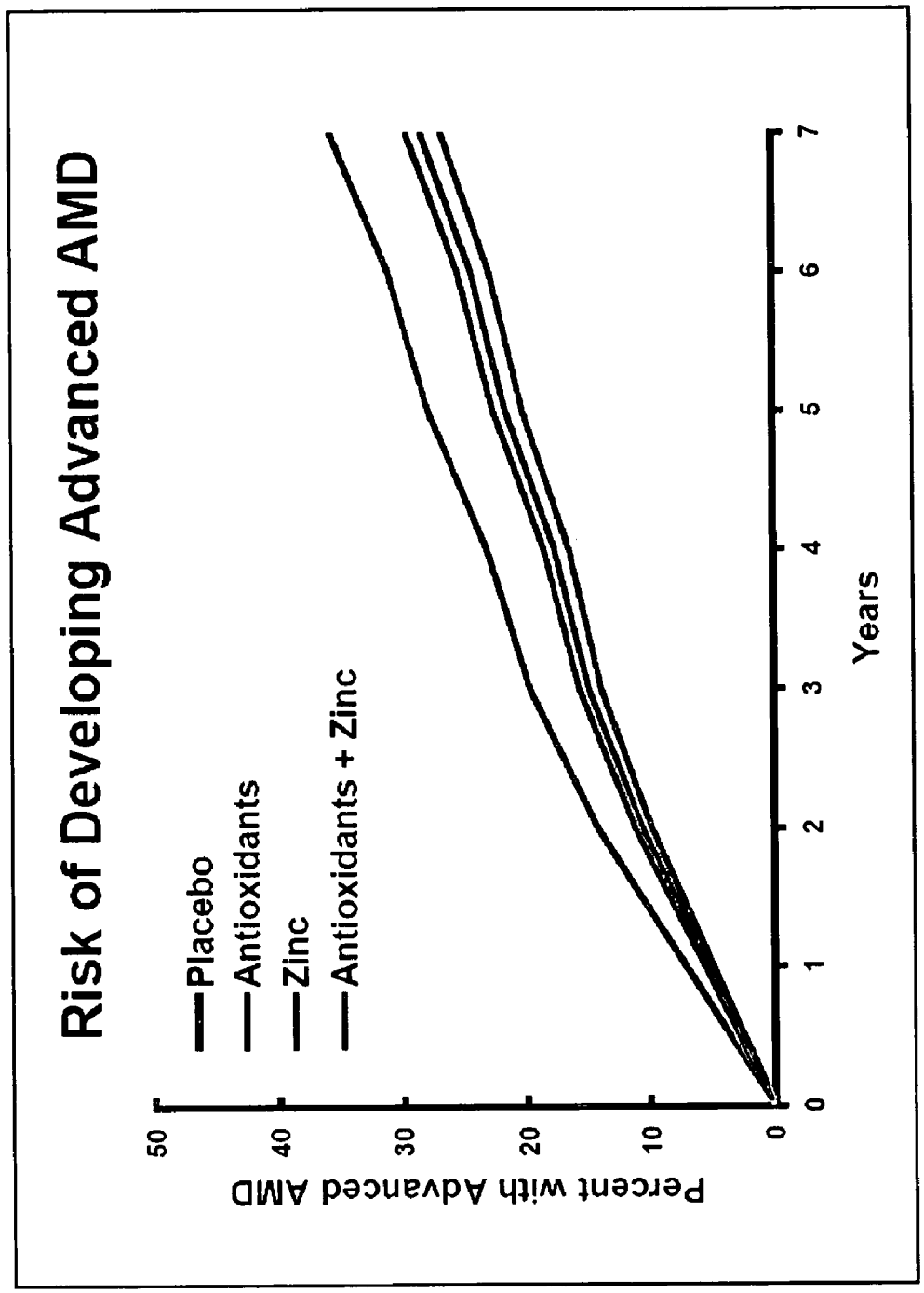
FIG. 6. Summary of Potential for Developing Severe AMD in AREDS Study. Line graph showing the percentage of patients who developed severe AMD over the 7-year course of the AREDS Study in the four Study Groups evaluated.

It is clear that the MIRA-1 results derived from the use of the composition of the present invention is superior to the results obtained in the AREDS trial; this despite the fact that the present invention incorporates some of the same ingredients as are used in the AREDS formulation. Thus, based on these two government-sponsored studies there is clearly a measurable benefit in visual function bestowed by unexpected synergism provided by the effective amounts of the combination of ingredients of the present invention as compared to the AREDS formulation. FIG. 6 shows a line graph plot demonstrating the Risk of Developing Advanced AMD over time from the groups involved in the AREDS study.

A further object of the present invention is to provide a kit comprising a suitable container, the therapeutic of the invention in a pharmaceutically acceptable form disposed therein, and instructions for its use.

It is understood that the examples and embodiments described herein are for illustrative purposes only and that various modifications or changes in light thereof will be suggested to persons skilled in the art and are included within the spirit and purview of this application and are considered within the scope of the appended claims. For example, the relative quantities of the ingredients may be varied to achieve different desired effects, additional ingredients may be added, and/or similar ingredients may be substituted for one or more of the ingredients described.

TABLE 1

Example of the Dietary Supplement of the Invention; Unit Dosage, Daily Dosage, and Daily Dosage Ranges According to the Present Invention.

| Component | mg/cap | Effective dose/cap | % by weight | Caps per day | Daily Dose (preferred embodiment) | Range (per day) |
|---|---|---|---|---|---|---|
| Vitamin A (Retinyl palmitate) | 2.5 mg/cap [250 IU/mg] | 625 IU/cap | 0.438% | 4 | 2500 IU | 2500-6000 IU [10-24 mg] |
| beta-Carotene (betatene 7.5%) | 5.252 mg/cap [119 IU/mg] | 625 IU/cap | 0.92% | 4 | 2500 IU (25 mg) | (between b-Carotene and vit A: 2500-6000 IU of vit A) |
| Vitamin E (d,l-alpha-tocopherol) | 133.3 mg/cap [.75 IU/mg] | 100 IU/cap | 23.352% | 4 | 400 IU (533.2 mg) | 50-800 IU [66.7-1066.7 mg] |
| Vitamin C (ascorbic acid) | 131.579 mg/cap | 131.579 mg/cap | 23.051% | 4 | 526 mg | 400-2000 mg |
| Zinc (zinc ascorbate 20%) | 100 mg/cap of Zn As Zn Ascorbate. | 20 mg/cap Zn | 17.518% | 4 | 80 mg | 50-200 mg |
| Copper (copper gluconate 14%) | 3.571 mg/cap | 0.5 mg/cap Cu | 0.626% | 4 | 2 mg | 1-4 mg |

TABLE 1-continued

Example of the Dietary Supplement of the Invention; Unit Dosage, Daily Dosage, and Daily Dosage Ranges According to the Present Invention.

| Component | mg/cap | Effective dose/cap | % by weight | Caps per day | Daily Dose (preferred embodiment) | Range (per day) |
|---|---|---|---|---|---|---|
| Selenium (selenium acid chelate 0.2%) | 0.875 mg/cap | 17.5 ug/cap | 0.153% | 4 | 70 ug | 50-100 ug |
| Lutein (5% FloraGlo) | 75 mg/cap | 3.75 mg/cap | 13.139% | 4 | 15 mg | 10-20 mg |
| Zeaxanthin (5%) | 3.75 mg/cap | 0.188 mg/cap | 0.657% | 4 | 1 mg | 0.5-4 mg |
| Bilberry Extract (assorted flavonoids) | 15 mg/cap | 15 mg/cap | 2.628% | 4 | 60 mg | 50-120 mg |
| Eye Bright (powder) (Tannins, Antioxidants) | 30 mg/cap | 30 mg/cap | 5.256% | 4 | 120 mg | 60-250 mg |
| Spinach (leaf powder) (antioxidants, vitamin C, E; K+, Mg, folic acid (B9)) | 17.495 mg/cap | 17.495 mg/cap | 3.065% | 4 | 70 mg | 30-100 mg |
| Alfalfa (grass powder) (Ca, K+, Fe, Mg, P; vit A, B6, D, K, E) | 10 mg/cap | 10 mg/cap | 1.752% | 4 | 40 mg | 20-80 mg |
| alpha-Lipoic Acid | 0.005 mg/cap | 0.005 mg/cap | 0.001% | 4 | 0.020 mg | 5-100 mcg |
| Citrus Bioflavonoid Complex (35%) | 12.5 mg/cap | 4.375 mg/cap | 2.19% | 4 | 18 mg | 10-50 mg |
| Cellulose Fiber (BH200) | 20 mg/cap | 20 mg/cap | 3.504% | 4 | 80 mg | Inert Matrix Ingredients 5-50% by weight |
| Magnesium (magnesium stearate) | 5 mg/cap | 5 mg/cap | 0.876% | 4 | 20 mg | |
| Silica (inert matrix) | 5 mg/cap | 5 mg/cap | 0.876% | 4 | 20 mg | |
| Total | 571 mg | | 100% | | | |

What is claimed is:

1. A dietary supplement composition for improving retinal health comprising:
   from about 0.3% to about 1% by weight of vitamin A, as retinyl palmitate;
   from about 0.5% to about 1.5% by weight of beta-carotene;
   from about 15% to about 30% by weight of vitamin E, as d,l-alpha tocopherol;
   from about 15% to about 30% by weight of vitamin C;
   from about 10% to about 25% by weight of zinc, as zinc ascorbate;
   from about 0.1% to about 1% by weight of copper, as copper gluconate;
   from about 0.05% to about 0.5% by weight of selenium, as selenium acid chelate;
   from about 2.0% to about 20% by weight of lutein;
   from about 0.1% to about 1% by weight of zeaxanthin;
   from about 0.5% to about 5% by weight of bilberry extract;
   from about 1% to about 10% by weight of eyebright;
   from about 0.5% to about 5% by weight of spinach;
   from about 0.25% to about 2.5% by weight of alfalfa;
   from about 0.0001% to about 1.5% by weight of ALA;
   from about 0.5% mg to about 5% by weight of citrus bioflavanoid complex;
   from about 1% to about 5% by weight of cellulose fiber;
   from about 0.15% to about 1.5% by weight of magnesium; and
   from about 0.15% to about 1.5% by weight of silica.

2. The dietary supplement of claim 1, wherein the supplement further comprises at least one of a carrier, excipient, emulsifier, stabilizer, sweetener, flavoring agent, diluent, coloring agent, solubilizing agent or combinations thereof.

3. The dietary supplement of claim 2, wherein the supplement composition is formed into an orally ingestible dosage form to be taken daily.

4. The dietary supplement of claim 3, wherein the orally ingestible dosage form is selected from the group consisting of a capsule, tablet, caplet, softgel, sustained release tablet, enterically coated tablet, liquid, gel, powder, and any combination thereof.

5. The dietary supplement of claim 4, wherein the orally ingestible dosage form is divided into two or more daily dosage units.

6. The dietary supplement of claim 5, wherein the daily dosage units comprise two doses of two capsules per dose.

7. A dietary supplement comprising, on a daily dosage basis:
   from about 4500 IU to about 5500 IU of vitamin A;
   from about 100 IU to about 600 IU vitamin E;
   from about 500 mg to about 1000 mg of vitamin C;
   from about 70 mg to about 100 mg of zinc;
   from about 1.5 mg to about 3.5 mg of copper;
   from about 60 μg to about 100 μg of selenium;
   from about 10 mg to about 20 mg of lutein;
   from about 0.5 mg to about 3 mg of zeaxanthin;
   from about 55 mg to about 100 mg of bilberry extract;
   from about 100 mg to about 200 mg of eyebright;
   from about 40 mg to about 80 mg of spinach;
   from about 30 mg to about 60 mg of alfalfa;
   from about 5 μg to about 60 μg ALA;
   from about 15 mg to about 45 mg of citrus bioflavonoid complex;
   from about 60 mg to about 100 mg of cellulose fiber;
   from about 10 mg to about 40 mg of magnesium; and
   from about 15 mg to about 35 mg of silica.

8. The dietary supplement of claim 7, wherein the supplement further comprises at least one of a carrier, excipient, emulsifier, stabilizer, sweetener, flavoring agent, diluent, coloring agent, solubilizing agent or combinations thereof.

9. The dietary supplement of claim 8, wherein the supplement composition is formed into an orally ingestible dosage form to be taken daily.

10. The dietary supplement of claim 9, wherein the orally ingestible dosage form is selected from the group consisting of a capsule, tablet, caplet, softgel, sustained release tablet, enterically coated tablet, liquid, gel, powder, and any combination thereof.

11. A method of improving retinal health comprising the steps of:
providing an effective amount of the dietary supplement of claim 1 divided into one or more dosage units; and
administering the dietary supplement to an individual in need thereof.

12. A method of treating vision impairment comprising the steps of:
providing an effective amount of the dietary supplement of claim 1 divided into one or more dosage units; and
administering the dietary supplement to an individual in need thereof.

13. A method of treating macular degeneration comprising the steps of:
providing an effective amount of the dietary supplement of claim 1 divided into one or more dosage units; and
administering the dietary supplement to an individual in need thereof.

14. A dietary supplement composition for the improvement of retinal health comprising, on a daily dosage basis:
about 5000 IU of vitamin A;
about 400 IU vitamin E;
about 526 mg of vitamin C;
about 80 mg of zinc;
about 2 mg of copper;
about 70 µg of selenium;
about 15 mg of lutein;
about 1 mg of zeaxanthin;
about 60 mg of bilberry extract;
about 120 mg of eyebright;
about 70 mg of spinach;
about 40 mg of alfalfa;
about 20 µg ALA;
about 18 mg of citrus bioflavanoid complex;
about 80 mg of cellulose fiber;
about 20 mg of magnesium; and
about 20 mg of silica.

* * * * *